United States Patent [19]

Hoenig et al.

[11] 4,323,064
[45] Apr. 6, 1982

[54] VOLUME VENTILATOR

[75] Inventors: Richard J. Hoenig, Coopersburg; James J. Klinikowski, Whitehall, both of Pa.

[73] Assignee: Puritan-Bennett Corporation, Kansas City, Mo.

[21] Appl. No.: 44,635

[22] Filed: Jun. 1, 1979

Related U.S. Application Data

[63] Continuation of Ser. No. 735,369, Oct. 26, 1976, abandoned.

[51] Int. Cl.³ .............................................. A61M 16/00
[52] U.S. Cl. .......................... 128/204.21; 128/202.22; 128/205.24
[58] Field of Search ...................... 128/204.21, 204.22, 128/204.23, 205.24, 204.24; 340/214

[56] References Cited

U.S. PATENT DOCUMENTS

| | | | |
|---|---|---|---|
| 3,831,596 | 8/1974 | Cavallo | 128/204.23 |
| 3,905,362 | 9/1975 | Eyrick et al. | 128/204.21 |
| 3,911,899 | 10/1975 | Hattes | 128/205.23 |
| 3,961,627 | 6/1976 | Ernst et al. | 128/204.21 |
| 3,972,327 | 8/1976 | Ernst et al. | 128/204.21 |
| 4,001,700 | 1/1977 | Cook et al. | 128/DIG. 7 |
| 4,003,377 | 1/1977 | Dahl | 128/204.23 |

FOREIGN PATENT DOCUMENTS

| | | | |
|---|---|---|---|
| 2301967 | 9/1976 | France | 128/204.21 |
| 1364641 | 8/1974 | United Kingdom | 128/204.21 |

Primary Examiner—Henry J. Recla
Attorney, Agent, or Firm—Allan Ratner

[57] ABSTRACT

A volume ventilator having a plurality of integrated modes of operation for providing a patient with a flow of breathing gas under pressure. A plurality of adjustable setting devices each producing an individual threshold signal related to a parameter of the gas flow. Mode switching means provides for the selection of at least one mode signal. Each threshold signal is compared with a common variable signal for producing a plurality of control signals. At least one of the control signals is selected in accordance with the selected mode signal and that control signal is applied to a valve system for controlling flow of gas to the patient. In this manner, the setting devices may be continuously adjusted to change one or more of the threshold signals without varying any of the other threshold signals. There is further provided a comprehensive system of alarms.

44 Claims, 19 Drawing Figures

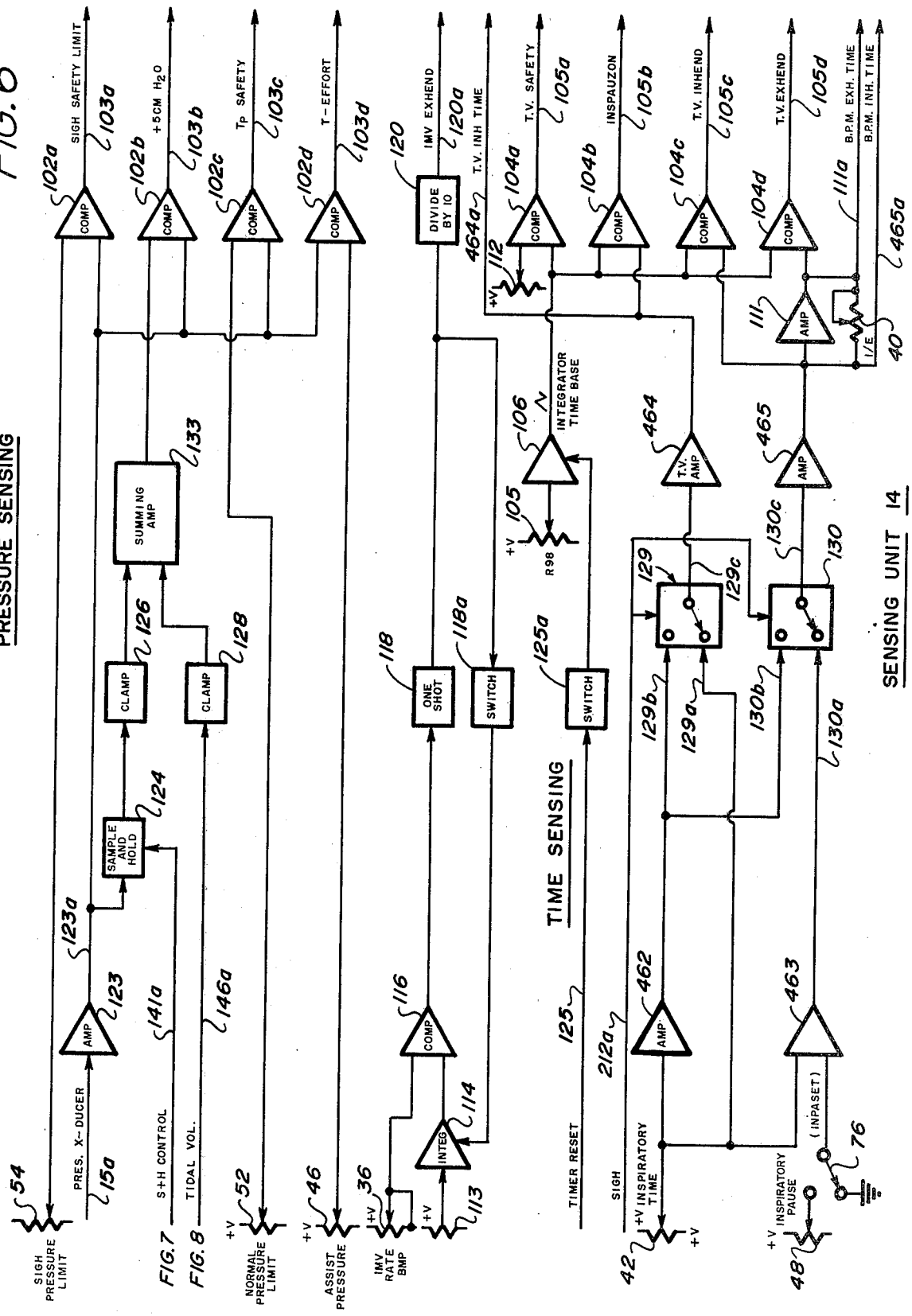

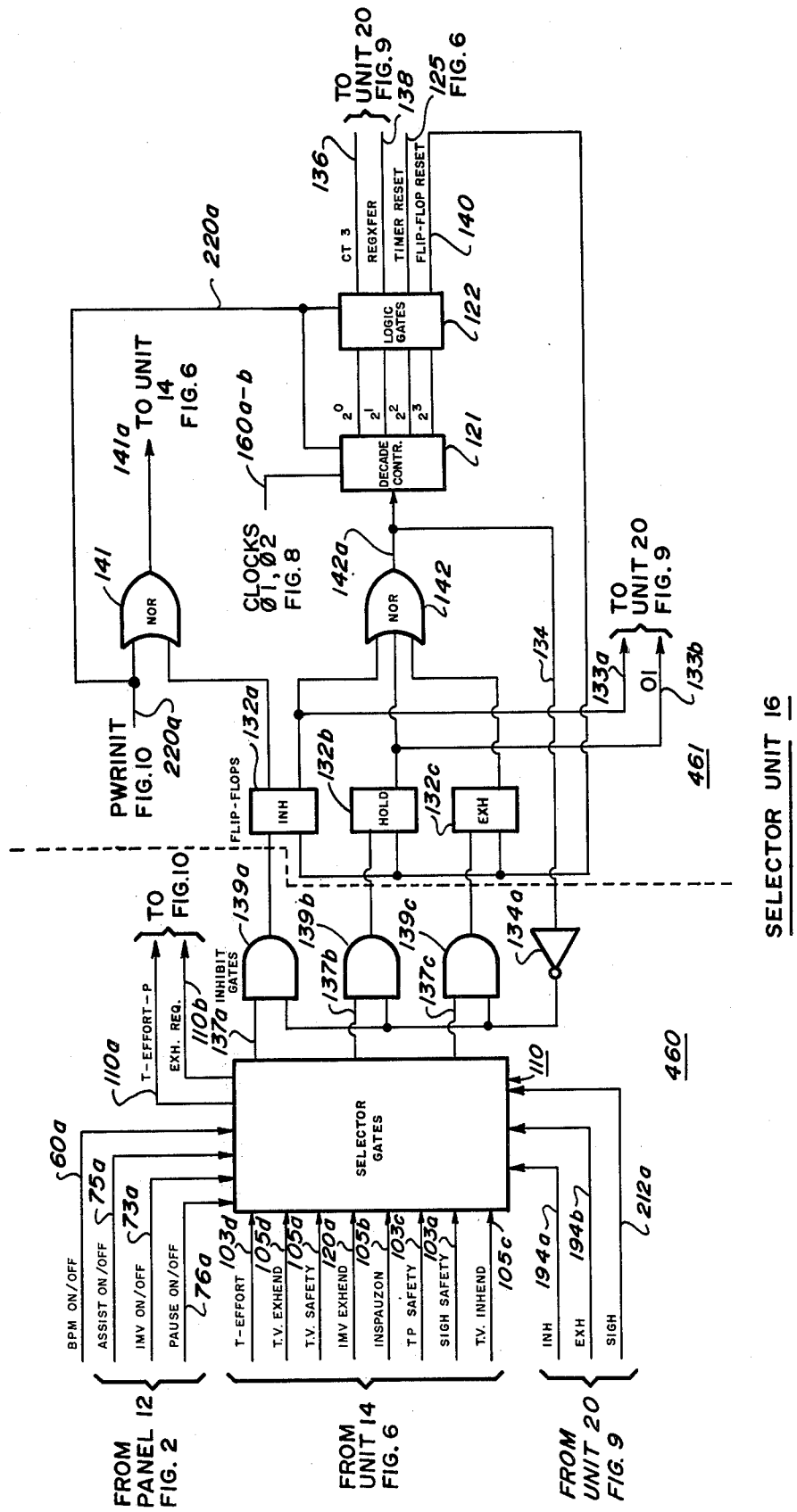

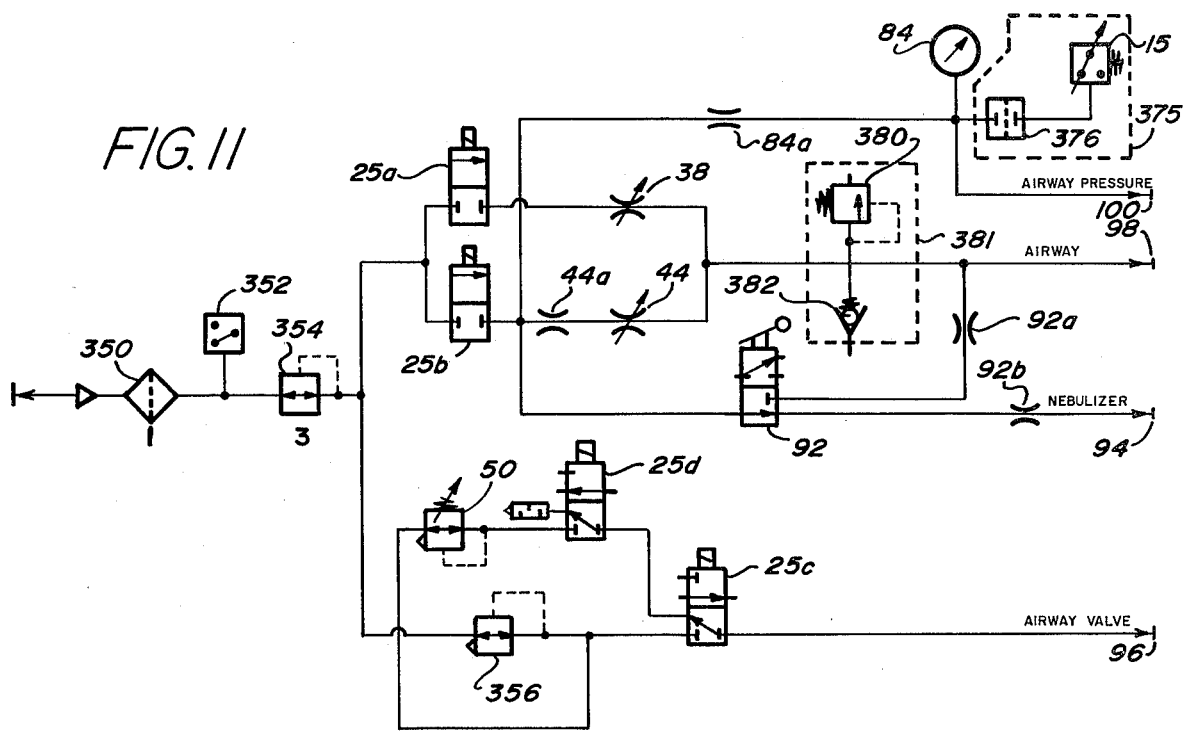
FIG. 11
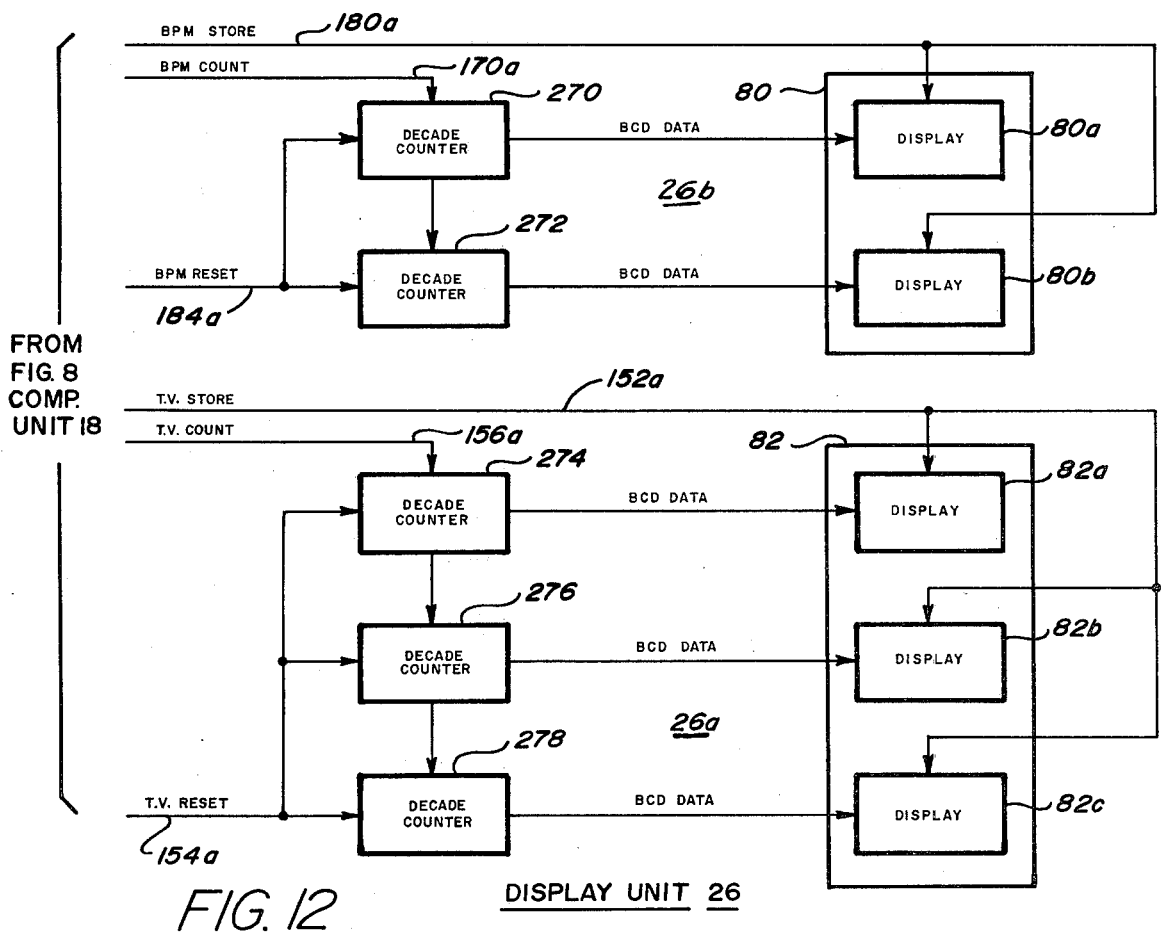
FIG. 12   DISPLAY UNIT 26

LOGIC GATES 122

CONSOLE ALARM UNIT 28

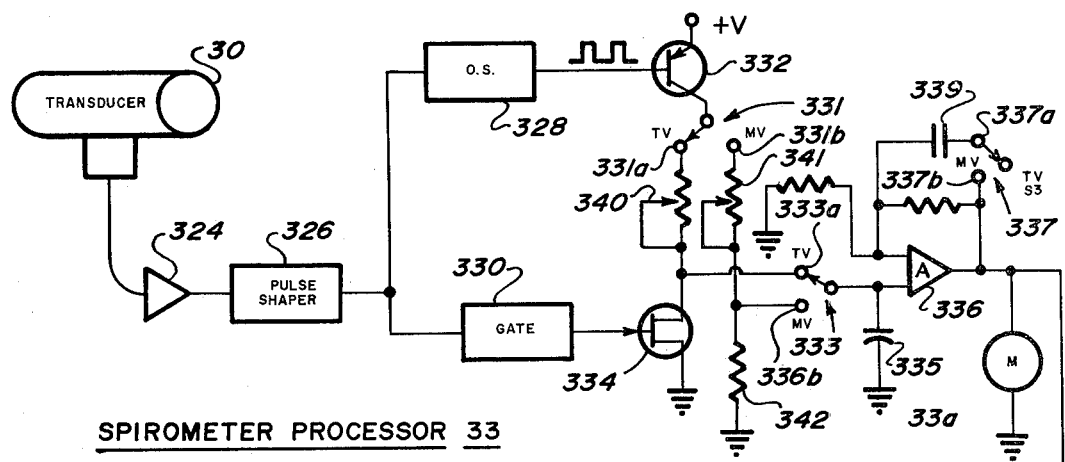
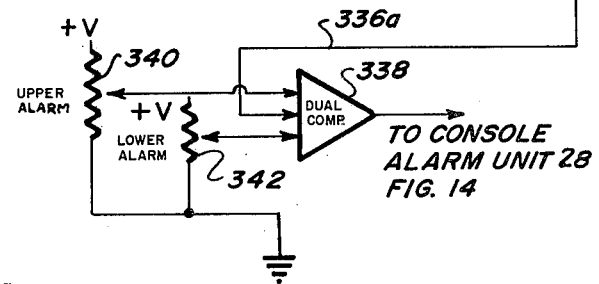
FIG. 15
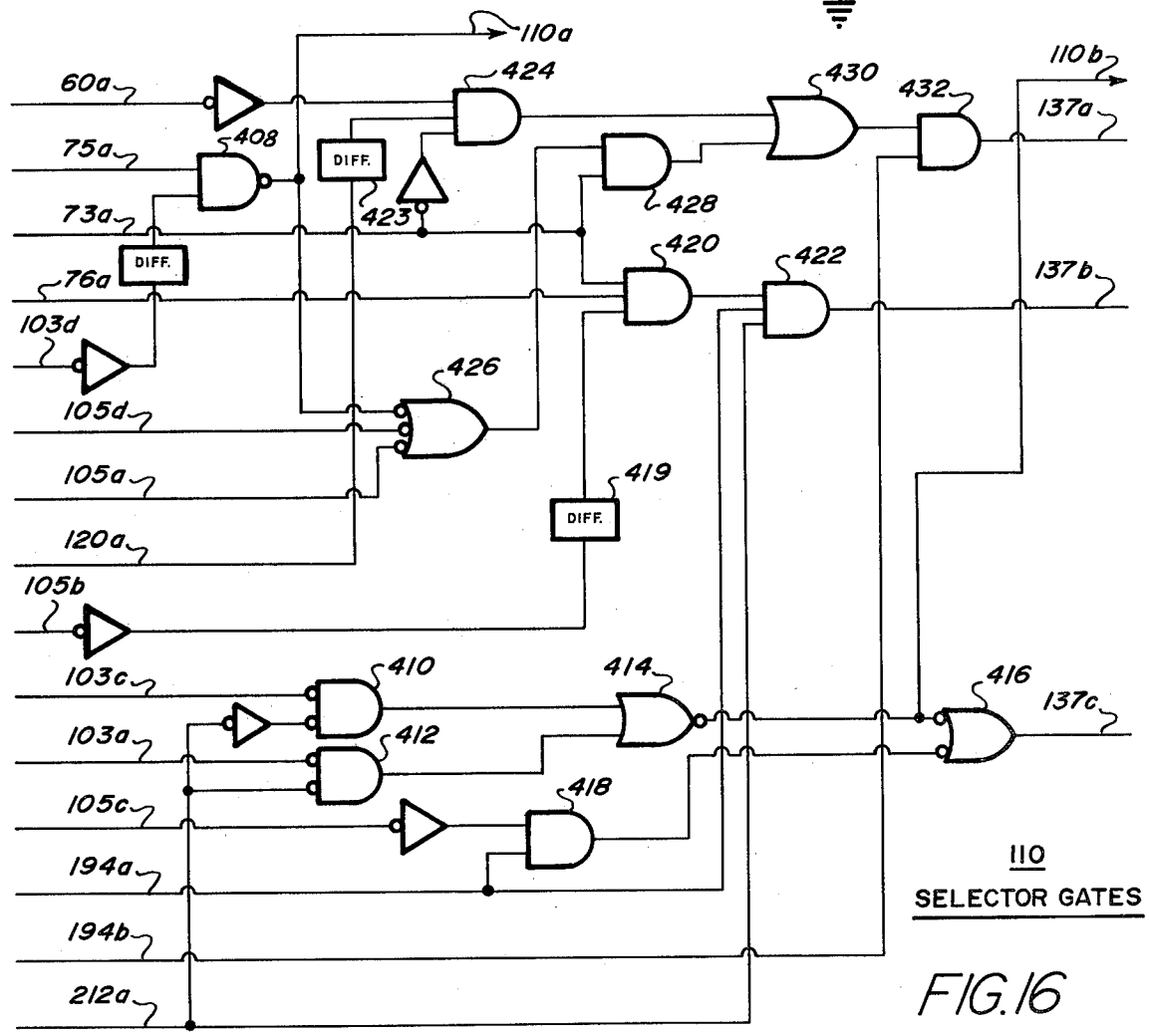
FIG. 16

LOGIC GATES

VOLUME VENTILATOR

This is a continuation, of application Ser. No. 735,369, filed Oct. 26, 1976 now abandoned.

TABLE OF CONTENTS

ABSTRACT OF THE DISCLOSURE
BACKGROUND OF THE INVENTION
  A. FIELD OF THE INVENTION
  B. PRIOR ART
SUMMARY OF THE INVENTION
BRIEF DESCRIPTION OF THE DRAWINGS
DETAILED DESCRIPTION
  I. GENERAL ORGANIZATION OF VENTILATOR
  II. SYSTEM DESCRIPTION
  III. DETAILED EXPLANATION OF UNITS
    A. SENSING UNIT 14
      1. Pressure Sensing
      2. Time Sensing
    B. SELECTOR UNIT 16
    C. PROCESSOR UNIT 20
    D. CONTROLLER PNEUMATIC UNIT
    E. COMPUTER UNIT 18
    F. DISPLAY UNIT 26
    G. CONTROL ALARM UNIT 22
    H. CONSOLE ALARM UNIT 28
    I. SPIROMETER PROCESSOR 33
  IV. DETAILED EXPLANATION OF GATES
    A. LOGIC GATES 122—FIG. 3
    B. SELECTOR GATES 110—FIG. 16
    C. DRIVE GATE 196—FIG. 17
    D. COUNT GATES 210, 214—FIG. 18
    E. LOGIC GATES 152—FIG. 19
  V. TABLE OF COMPONENTS

BACKGROUND OF THE INVENTION

A. FIELD OF THE INVENTION

This invention relates to the field of art of volume ventilators.

B. PRIOR ART

For respiratory ailments such as lung disease, chest injury and muscular disease, it has been necessary to ventilate the lungs of a patient by artifical means. Such intensive respiratory care has been provided by volume ventilators. However, prior volume ventilators have had drawbacks in providing a high degree of accuracy, predictability, and independence in controlling differing parameters as sigh, assist, inspiratory pause, etc. There has in the past been an interaction between individual settings so that when one control setting of a parameter has been adjusted, there has been undesirable changes in one or more other settings. As a result, when making a single setting change, most of the other settings were required to be checked and appropriate re-settings made.

A further drawback in prior volume ventilators has been the lack of integrating the many modes of operation in one unitary system and particularly integrating the IMV mode. Still further, prior ventilators left much to be desired in detecting malfunctions and providing alarms. There has not been a comprehensive system of alarms which would indicate failure in the electronics, in the pneumatics and in the circuit to the patient. cl

SUMMARY OF THE INVENTION

A ventilator system having a plurality of integrated modes of operation for providing a patient with a flow of breathing gas under pressure in which there is mode selection logic for selecting the integrated modes corresponding to sigh, assist, inspiratory pause and PEEP. A valve system controls the flow of gas to the patient connection means through which the patient inspires and expires. A plurality of adjustable setting means provide individual predetermined threshold signals related to the gas flow parameters of the integrated modes. A signal sensing system compares each threshold signal to a reference signal for providing a plurality of control signals to the valve system. The signal sensing system produces a common signal that changes in value over time as a function of the patient's respiratory activity. At least one of the control signals is selected responsive to the mode selection logic for controlling the flow of gas through the valve means to the patient connection means whereby the setting means may be continuously adjusted to change one or more of the threshold signals without varying any of the other threshold signals.

BRIEF DESCRIPTION OF THE DRAWINGS

FIG. 6 illustrates in more detail and in block diagram from the sensing unit of FIGS. 5A-B;

FIG. 7 illustrates in more detail and in block diagram form the selector unit of FIGS. 5A-B;

FIG. 11 is a schematic drawing of the pneumatic control unit of FIG. 4;

FIG. 12 illustrates in more detail and in block diagram form the display unit of FIGS. 5A-B;

FIG. 15 illustrates in more detail and in block diagram form the spirometer processor of FIGS. 5A-B;

FIG. 16 illustrates the detailed block diagram of the selector gates of the selector unit of FIG. 7;

DETAILED DESCRIPTION

I. GENERAL ORGANIZATION OF VENTILATOR

Figure 1:
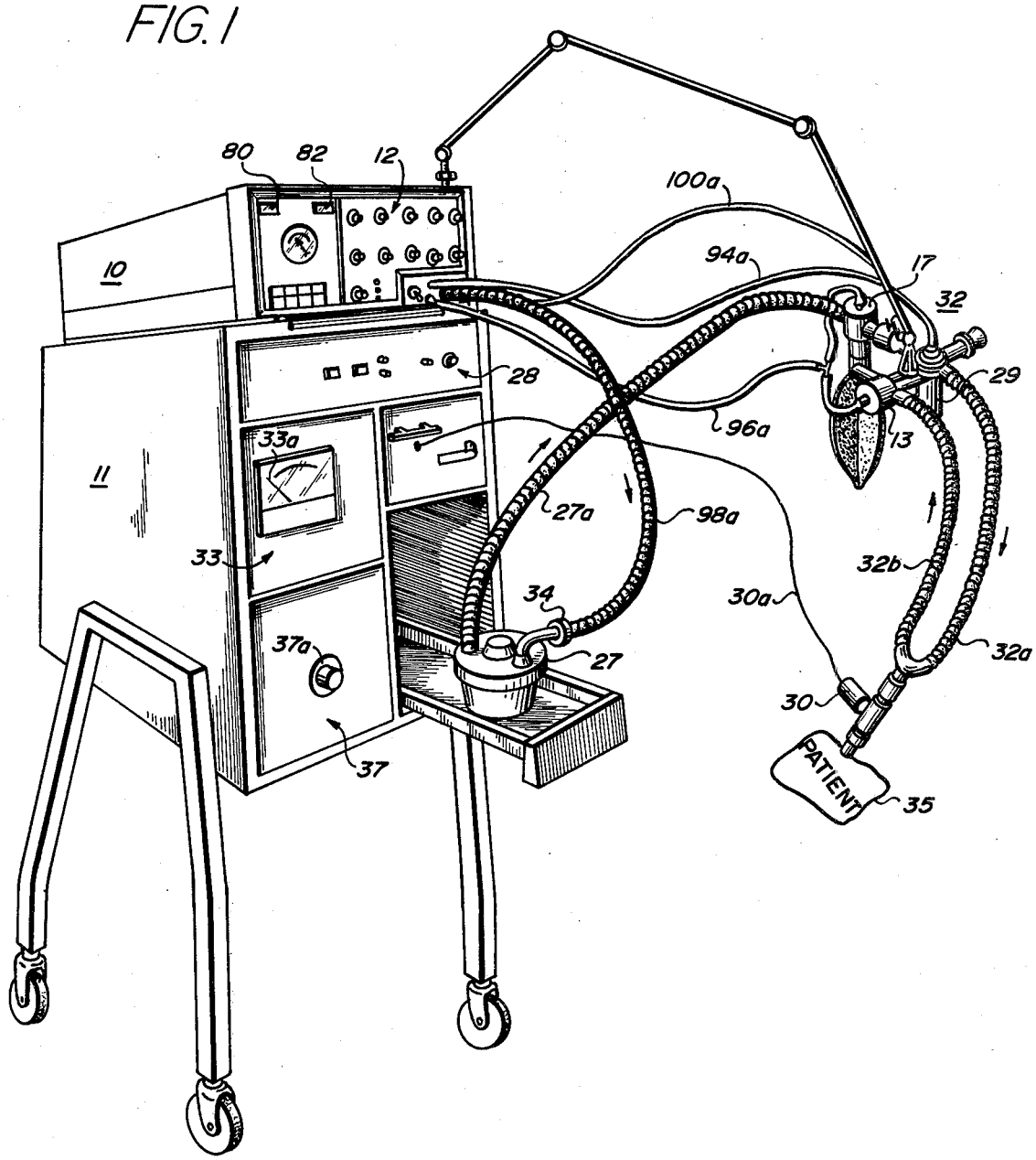
FIG. 1 illustrates a perspective view of a volume ventilator embodying the present invention.

As shown in FIG. 1, the volume ventilator is effective to independently control vital respiratory parameters in artificial administration of respiration such as sigh, assist pressure, inspiratory pause, positive end expiratory pressure (PEEP), continuous positive airway pressure (CPAP) and auxiliary functions. The ventilator comprises a control unit 10, a console unit 11 and a patient circuit 32. Control unit 10 performs electronic control and computation as well as pneumatic control and regulation.

Figure 2:
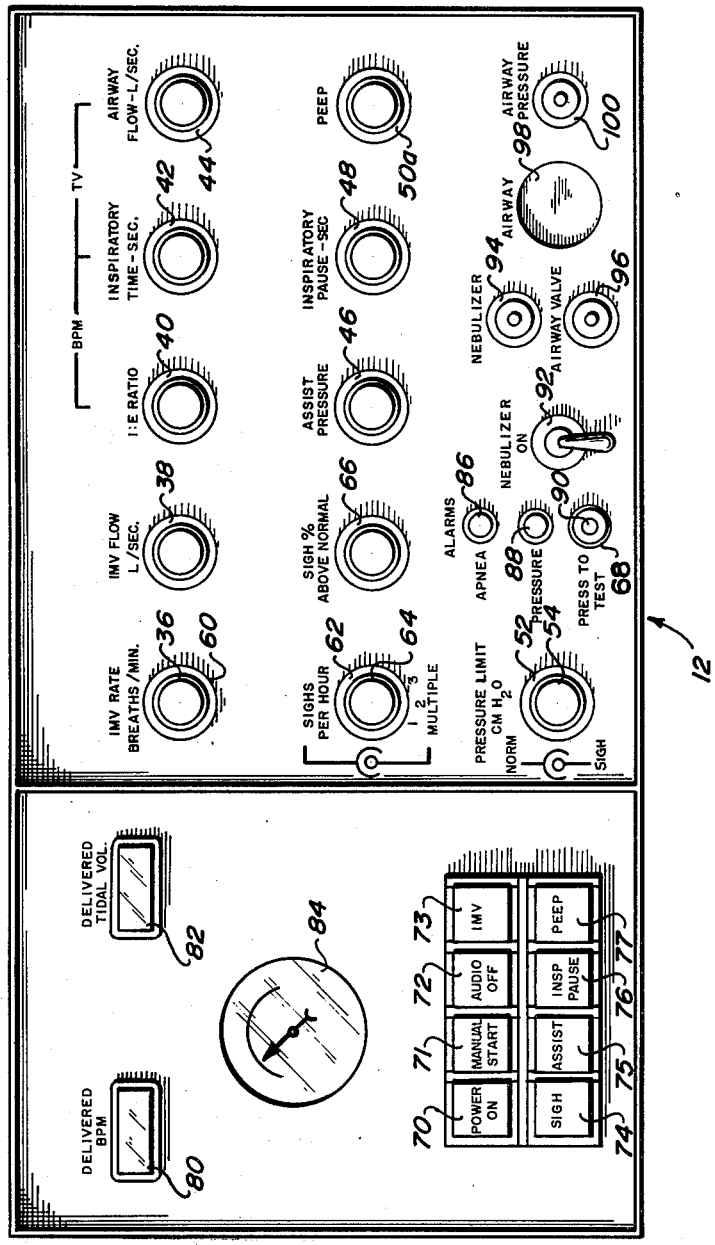
FIG. 2 illustrates in more detail the front panel of the volume ventilator of FIG. 1.

The electronic control includes operator adjusted knobs and switches to allow selection and setting of various parameters such as pressure, breathing rate, volume, etc. These are on the front panel 12 as shown in FIG. 2 which also contains two digital displays 80, 82 indicating delivered breaths per minute (BPM) and delivered tidal volume (TV) respectively. In addition, gauge 84 on front panel 12 indicates airway pressure of patient circuit 32. There is further provided alarm indicators and fittings for input/output airway tubes which are connected to patient circuit 32.

The pneumatic portion of control unit 10 performs several functions. The primary functions of the pneumatic portion are to filter the incoming gases to control unit 10, regulate pressure and control flow into patient circuit 32. The main air flow from control unit 10 enters tube 98a at outlet fitting 98 and is passed through a humidifier 27 and then to an output tube 27a into a patient circuit 32.

Figure 3:
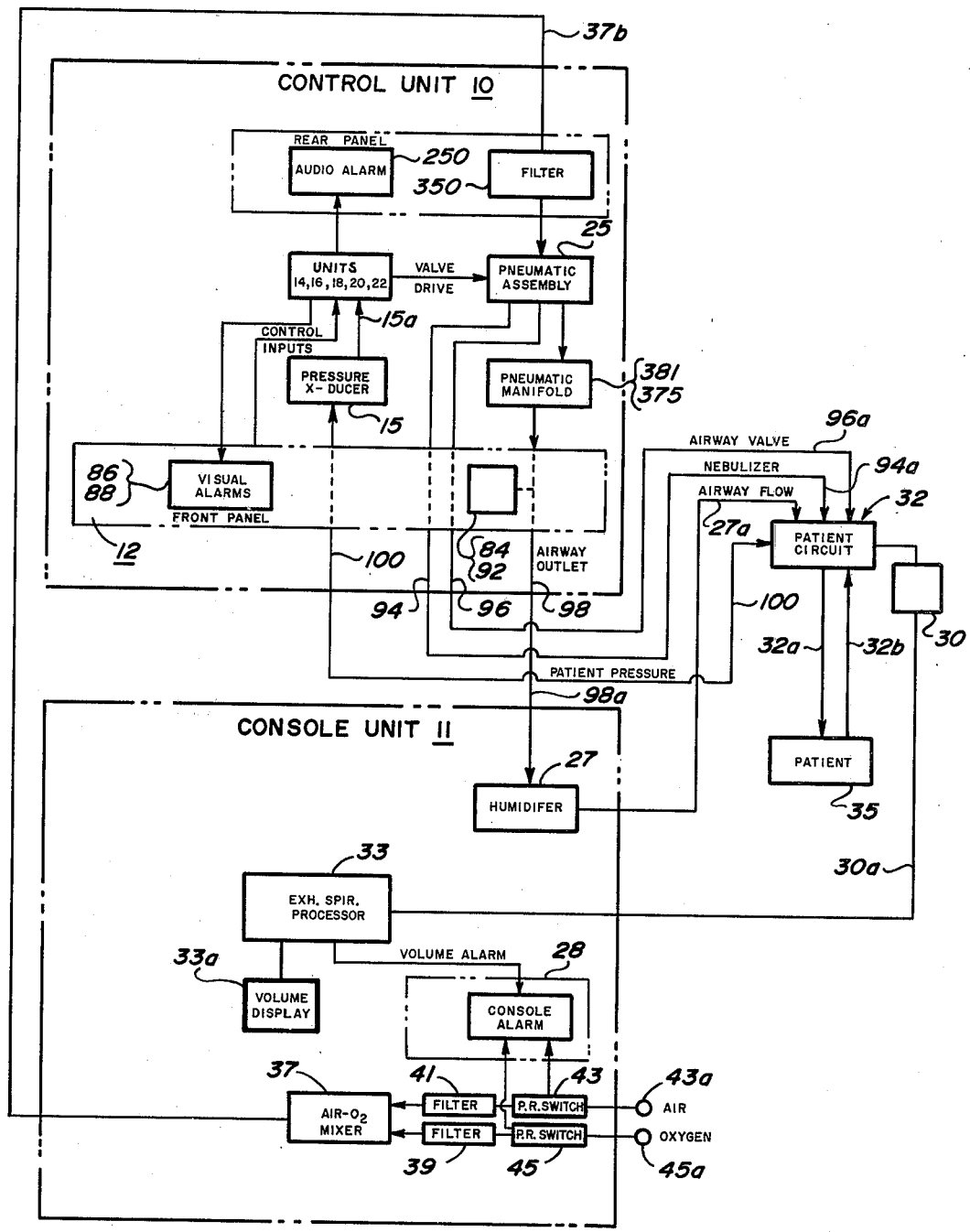
FIG. 3 illustrates the system block diagram of the volume ventilator of FIG. 1.

The pneumatic portion of control unit 10 includes a fitting 100 for an airway pressure tube 100a. Internal tubing from fitting 100, FIG. 2, is effective to transmit the patient circuit pressure to pressure gauge 84 on front panel 12. The airway pressure appearing at fitting 100 is also connected to a pressure transducer 15 internal to control unit 10 as shown in FIG. 3. The pneumatic circuit also includes a positive end expiratory pressure (PEEP) regulation circuit and a nebulizer control circuit.

Console unit 11 includes a console alarm 28, a spirometer processor 33, a volume display 33a and an air-oxygen mixer 37. Console alarm 28 determines if a pressure or volume setting has been exceeded and produces an audible and visual alarm on the front panel of alarm unit 28.

Spirometer processor 33 receives an electrical signal from spirometer sensor 30 of patient circuit 32. Processor 33 computes the volume for each breath and the average volume per minute and displays a selected one of these computations on front panel meter 33a. Air-oxygen mixer 37 includes air and oxygen pressure switches and filters as well as a mixer which mixes the air and oxygen in a predetermined amount set by control 37a. The output of air-oxygen mixer 37 is coupled by way of line 37b (FIG. 3) to control unit 10 in the manner previously described.

Patient circuit 32 includes a main airway circuit having corrugated walled tubes 98a, 27a, 32a, and 32b as well as pressure sensing line 100a, valve control line 96a and nebulizer drive line 94a. The main airway circuit is supplied by way of connection to outlet fitting 98 in panel 12. The supplied air mixture passes through tubing 98a, bacteria filter 34, humidifier 27 and continues by way of tube 27a through intermittent mandatory ventilation (IMV) valve 17 to nebulizer 29. The air mixture continues through inhale tubing 32a, and a spirometer sensor 30 to patient 35. The exhale gases from patient 35 are in turn passed back through spirometer sensor 30 to exhale tubing 32b and then through airway valve 13 to the atmosphere. Nebulizer 29 is controlled by way of line 94a coupled to a fitting 94 on the front panel 12. IMV valve 17 and airway valve 13 are controlled by way of line 96a connected to the pneumatic portion of the control unit 10 at a front panel inlet 96.

II. SYSTEM DESCRIPTION

Basic system elements are shown in somewhat greater detail in FIG. 3 where the connections between control unit 10, console unit 11 and patient circuit 32 are illustrated. Specifically, in FIG. 3, the air and oxygen supplies are coupled to terminals 43a and 45a respectively. The air and oxygen pass through pressure switches 43 and 45 and through filters 41 and 39 respectively and into an air oxygen mixer 37. The function of pressure switches 43 and 45 is to supply low pressure alarm signals to alarm panel 28 to be displayed on the front panel of console 11. Filters 41 and 39 provide filtration of particulate matter in the air and oxygen supplies. Air oxygen mixer 37 is controlled by a control knob 37a as shown in FIG. 1.

Figure 4:
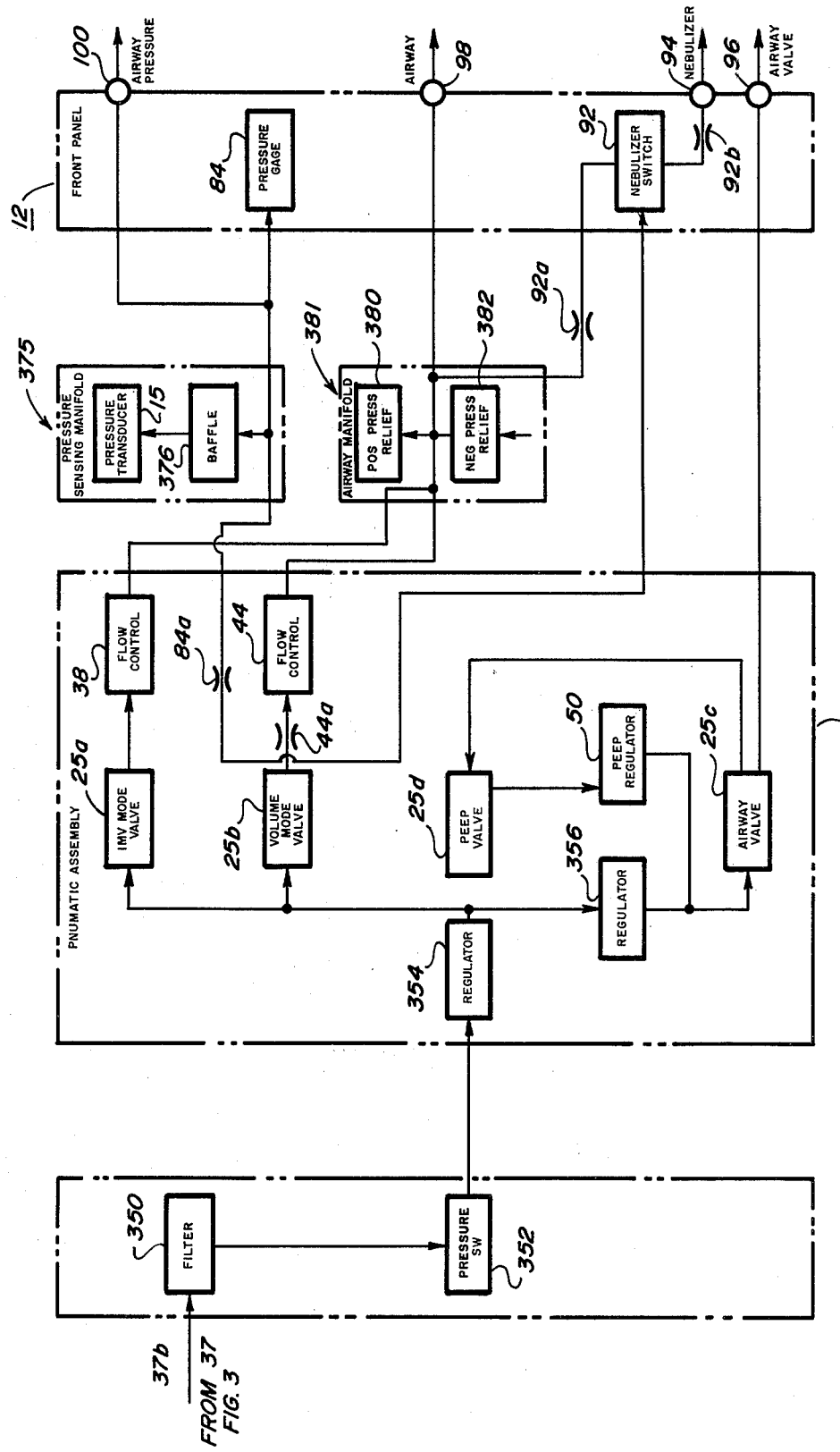
FIG. 4 illustrates in basic block diagram from the pneumatic controller unit of FIG. 1.

The output of the mixer 37 is connected by way of line 37b to a filter unit 350 located in control unit 10. The function of filter 350 is to provide additional filtering of the incoming air oxygen mixture. This filter 350 also provides for filtration when control unit 10 is fed from other supply sources which may be unfiltered. The output of filter 350 is fed to a pneumatic assembly 25 controlled by electronic units 14, 16, 18, 20 and 22. These electronic units provide the logical sequence of closing and opening of the solenoid valves 25a-d (FIG. 4) located in pneumatic assembly 25 as will later be described. The output of pneumatic assembly 25 is connected to pressure sensing manifold 375 and airway manifold 381 as shown in FIG. 4. Airway manifold 381 contains pressure release valves 380, 382 for the positive and negative pressure limits. Airway manifold 381 is connected to outlet fitting 98, FIG. 2.

The pressure in the patient circuit is transmitted by way of line 100a to fitting 100 on the front panel 12. Fitting 100 is connected by way of air baffle 376 to an internal pressure transducer 15, FIG. 4. The output of the pressure transducer 15 is an electronic signal which is fed by way of line 15a, FIG. 3, to the electronic units. Any malfunction as indicated by abnormal changes in pressure in pneumatic assembly 25 of patient circuit 32 is displayed by visual alarms 86, 88, FIG. 2, and a rear panel alarm 250 of control unit 10, FIG. 3.

Nebulizer 29 in patient circuit 32 is controlled by way of line 94a connected to front panel fitting 94, FIG. 2. Fitting 94 is connected internally to pneumatic assembly 25 which in turn is controlled by electronic units shown in FIG. 3. Airway valve 13 (FIG. 1) in the patient circuit is controlled by line 96a coupled to fitting 96 on panel 12. Fitting 96 also is internally connected to pneumatic assembly 25. Patient circuit 32 is connected by way of lines 32a, b and "Y" piece to the patient 35. Spirometer sensor 30 on the patient circuit measures the patient's exhalation flow. The output of spirometer sensor 30 is connected by way of wire 30a to processor 33 located in the console unit 11 as shown in FIG. 3.

The output of the processor unit 33 is displayed on a front panel meter 33a. The output of the processor unit 33 is also connected to alarm unit 28 which provides a front panel audio and visual alarm to indicate a low volume condition.

In addition to the pneumatic fittings 94, 96, 98 and 100, front panel 12 has several variable controls, switches, digital display and an analog pressure display 84. The variable controls on front panel 12 allow independent adjustment of pressure, time and flow. A subgroup of sigh controls allow the frequency and depth of sigh breaths to be set. Assist pressure control 46 and PEEP pressure control 50a are uncalibrated controls and are monitored by reading the pressure on gauge 84.

Figure 5A:
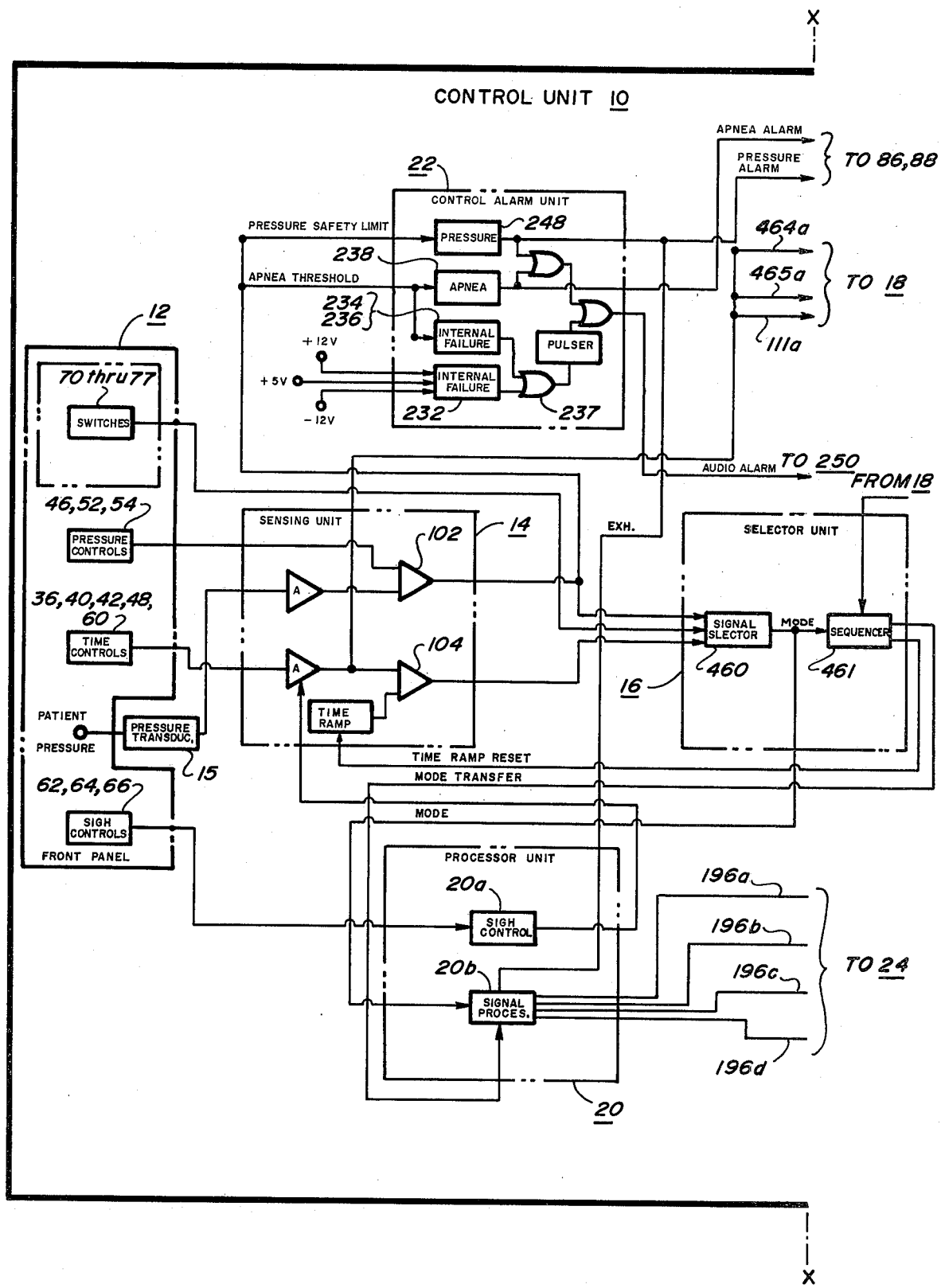
FIGS. 5A-B taken together illustrate in basic block form the electronic control diagram of control unit 10 and console unit 11 of the volume ventilator of FIGS. 1-4.
Figure 5B:
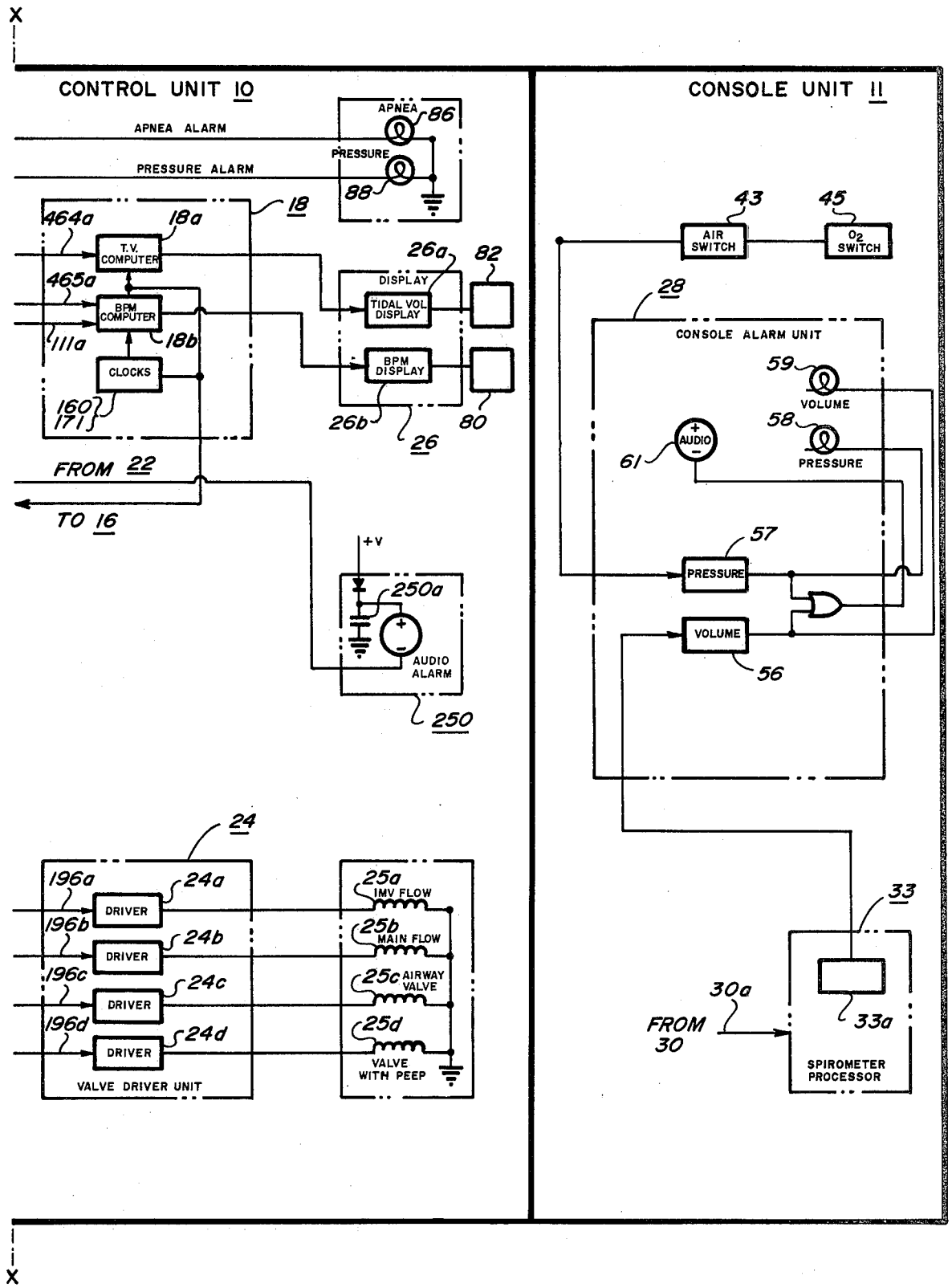

Pressure limit controls 52 and 54 are calibrated controls and provide a voltage comparison signal to a comparator located in the electronic portion of the control unit control logic in unit 14, FIGS. 5A-B. The outputs of controls 52, 54 are compared with a signal from pressure transducer 15. The IMV flow and the airway flow respectively are controlled by calibrated pneumatic controls 38 and 44, FIG. 2, respectively.

IMV rate control 36, inspiratory time control 42, inspiratory pause control 48 and I:E ratio control 40 provide time related threshold voltage variations which are compared against an internally generated time signal in the form of a ramp (a periodic signal which increases linearly with time) as shown in sensing unit 14 of control unit 10. The signals from these controls are applied to an independent set of comparators; and this independent comparison provides for mutual independence of these front panel controls. Output quantities such as BPM and TV are computed and displayed on front panel displays 80 and 82 respectively. These displays are based on values computed by computer unit 18 as a function of the settings of inspiratory time control 42, flow rate control 44 and I:E ratio control 40. The reading of tidal volume on display 82 may be crosschecked with readings of meter 33a which indicates the actual patient exhaled tidal volume and minute volume.

Similarly, it should be noted that the pressure related threshold signals from controls 46, 52 and 54 are applied to an independent set of comparators which compares all of them to the output of pressure transducer 15. The resultant signals are used for selection of different modes of operation. This provides for mutual independence of control of controls 46, 52 and 54. The actual patient pressure is displayed on display 84 and any difference between this reading and the pressure settings may be noted by the operator, and appropriate action taken.

Sigh-per-hour control 62, multiple-sigh control 64 and sigh-percent-above-normal control 66 supply signals to a processor unit 20 of control unit 10, FIGS. 5A-B. Nebulizer switch 92 is a toggle valve which admits the gas mixture from valve 25b to the nebulizer by way of fitting 94 as shown in FIG. 4. A push-to-test switch 90 and integral lamp 68 (FIG. 2) provide a signal to test and display if all alarms are working in a proper fashion. Front panel switches 70-77 provide for initiation of signals which are used in selector unit 16, FIGS. 5A-B. These allow a selection of different modes of operation such as start, IMV mode, SIGH, etc.

FIG. 4 shows the pneumatic circuit of control unit 10. Output 37b of air-oxygen mixer 37 is connected to a filter 350 which is effective to filter incoming air to a 5 micron particle size. The output of filter 350 is connected through a pressure switch 352 to a regulator 354 in pneumatic assembly 25. Pressure switch 352 is actuated by any pressure below 20 PSIG to initiate low pressure alarms and regulator 354 regulates output pressure between 33 and 38 PSIG. This internal regulation is necessary to maintain a calibrated flow to patient circuit 32. The output of regulator 354 is coupled to solenoid valves 25a, 25b and low-pressure regulator 356.

In the IMV mode of operation selected by switch 73 in unit 12, IMV mode solenoid 25a is activated to allow air to pass to flow control 38 and thence to airway manifold 381. Airway manifold 381 is also supplied by volume mode solenoid valve 25b connected in series with volume flow control 44 in the volume mode of operation. Pressure in the airway manifold 381 is limited to a range of values set by a positive pressure relief valve 380 and a negative pressure relief valve 382. Air is conveyed from manifold 381 to front panel fitting 98, FIGS. 2, 4.

Air pressure fitting 100 is connected to pressure gauge 84 and to a pressure sensing manifold 375 having a damping baffle 376 and a pressure transducer 15. The output of transducer 15 is used as a comparator signal in sensing unit 14, FIGS. 5A-B. It is this pressure signal that is compared independently with the signals from pressure controls 46, 52 and 54 to produce control signals which are used for the various modes of control operations.

The output of the regulator 356 is connected to an airway solenoid valve 25c and also to a PEEP regulator 50 as shown in FIG. 4. PEEP regulator 50 is controlled by a front panel knob 50a, FIG. 2. Solenoid valves 25c,d are controlled by electrical signals derived from processor unit 20, FIGS. 5A-B. The purpose of the pneumatic loop through valve 25d and regulator 50 is to maintain positive pressure at the end of exhalation (PEEP). The pneumatic output of airway solenoid valve 25c is connected by way of fitting 96 on the front panel 12 in FIG. 2.

FIGS. 5A-B show the electronic control block diagram for control unit 10 and the console unit 11. As previously described, the front panel controls and switches in unit 12 are connected to sensing unit 14, selector unit 16 and processor unit 20. The pressure signals from controls 46, 52 and 54 are compared in comparators 102 against the output of pressure transducer 15.

The output of pressure comparators 102 are connected to a control alarm unit 22 and to a selector unit 16 as shown. The control alarm unit responds if pressure has exceeded the set limits or if the pressure has failed to increase by an amount proportional to tidal volume. The latter function is defined as apnea. The control alarm unit causes audible alarm 250 to sound and lights up visual alarms 86 and 88 on front panel 12. Alarm unit 22 also generates an alarm upon failure of any of the internal power supply voltages (+12 V, +5 V, −12 V) and generates a pulsating alarm.

Sensing unit 14 compares the voltages from front panel time controls 36, 40, 42, 48 and 60 with an internally generated ramp signal in comparators 104 the output of which are applied to a signal selector unit 460 in selector unit 16. Signal selector 460 selects appropriate time or pressure related digital signals from comparators 102 and 104 as commanded by switches 70-77. Buffered outputs from the time controls are also supplied to a computer unit 18 for the calculation of the tidal volume and BPM and the resulting signals are fed to a display unit 26 which generates readouts on front panel displays 82 and 80. Computer unit 18 is also controlled by sequencer 461 of selector unit 16. The sequencer is effective to reset the internal time ramp signal in sensing unit 14 as well as transfer the mode in the processor unit 20 as shown in FIGS. 5A-B. Processor unit 20 receives signals from the front panel controls 62, 64, 66 and generates valve operating signals which are amplified by valve driver unit 24 to energize solenoid valves 25b–d. It should be understood that the selection of the sequence of valve operation is controlled by the combined logic of selector unit 16 and processor unit 20 as determined by the settings of the front panel controls and switches.

Console unit 11 includes a console alarm unit 28 which receives signals from air pressure switch 43 and oxygen pressure switch 45. A low pressure sensed by switches 43 or 45 is effective to activate pressure unit 57 which in turn lights front panel pressure alarm indicator 58 and also activates audible alarm 61. The output of flow transducer 30 is processed in processor 33 and applied to a sensing unit 56 which in turn lights low volume alarm indicator 59 on the front panel as well as activating audible alarm 61. It is in this fashion that low air or oxygen pressure or low respiration minute volume is brought to the attention of the operator. Volume computations made by processor 33 are displayed on front panel meter 33a.

III. DETAILED EXPLANATION OF UNITS

A. SENSING UNIT 14

As shown in FIG. 6, sensing unit 14 comprises amplifiers and comparators which process the analog voltages from front panel 12 and pressure transducer 15. The functions of this sensing unit are determined by the settings of the various mode selector switches 70–77. The description of sensing unit 14 may be divided in two general functional areas: time sensing and pressure sensing.

1. Pressure Sensing

The output of pressure transducer 15 by way of line 15a is applied to a pressure amplifier 123. The output of pressure amplifier 123 is applied to four comparators 102a–d. As shown, outputs of sigh pressure limit control 54, the normal pressure limit control 52 and the assist pressure limit control 46 are connected to comparators 102a, 102c and 102d respectively. Each of these comparators produce a low signal when the threshold voltage set by respective control 54, 52 or 46 has been crossed by the pressure signal on line 123a. The output of comparator 102d is effective to initiate an inhalation when the voltage from assist control 46 is crossed, provided that the proper conditions are present at selector unit 16, namely, the ventilator must be in the exhale mode and assist function 75 must have been turned on.

Figure 10:
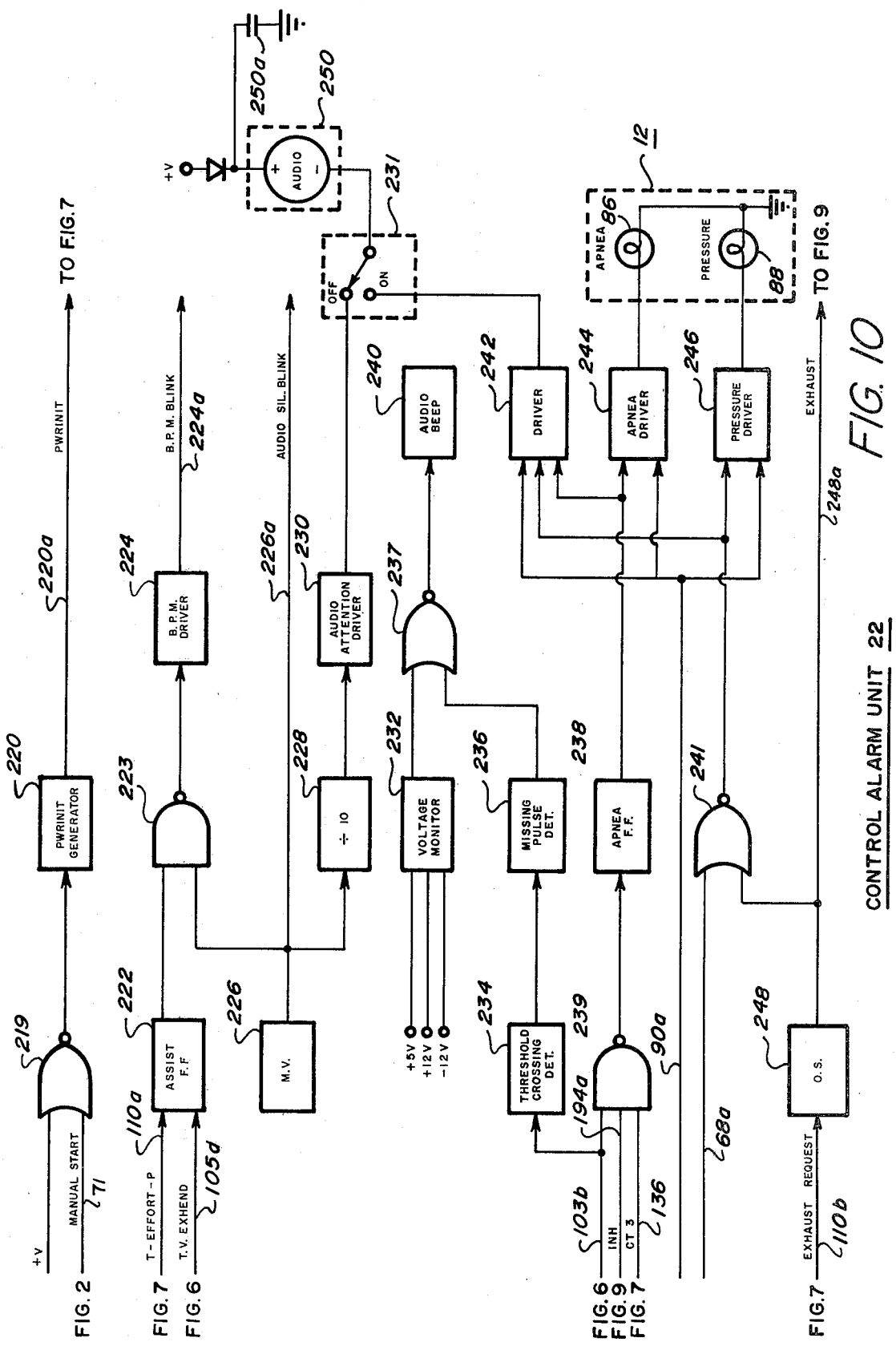
FIG. 10 illustrates in more detail and in block diagram form the control alarm unit of FIGS. 5A-B.
Figure 13:
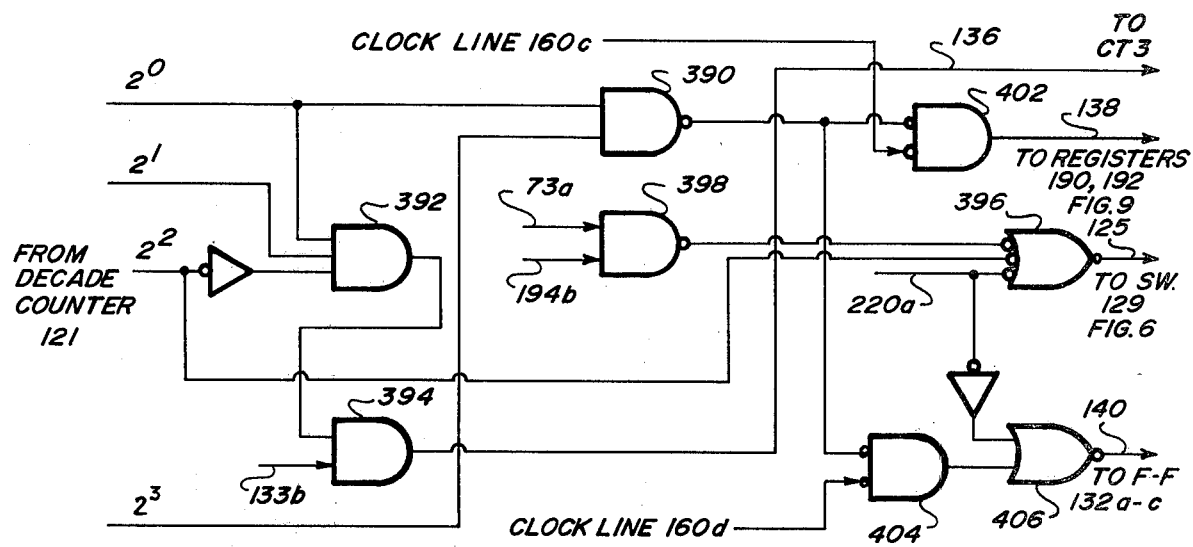
FIG. 13 illustrates the detailed block diagram of the logic gates of the selector unit of FIG. 7.

When the pressure signal on line 123a crosses the threshold set by controls 54 and 52, the outputs of comparators 102a and 102c generate low pulses on lines 103a and 103c respectively. These pulses are applied to a selector gate 110, FIG. 7, and, depending on mode conditions, are effective to produce an exhaust request signal on line 110b. As shown in FIG. 10, signal 110b is effective to produce a pulse with a duration of two seconds to turn on pressure alarm 250, light a front panel indicator 88 and open the breathing circuit valve 65 in order to release breathing circuit pressure.

The apnea threshold for comparator 102b in FIG. 6 changes proportionally with pressure and tidal volume setting. A sample and hold control signal is generated in selector unit 16 and is applied by way of line 141a to sample and hold circuit 124 as shown in FIG. 6. Circuit 124 is effective to sample the breathing circuit pressure at the beginning of each inhale cycle to establish a reference for pressure increase during inhalation.

The output of circuit 124 is clamped in unit 126 and applied to a summing amplifier 133. The tidal volume signal is derived from computer unit 18 and applied by way of line 146a to a clamp unit 128. The tidal volume signal is held to a minimum of 0.2 volts by clamp unit 128 which corresponds to 0.2 liter. Thus, only tidal volume exceeding 0.2 liter would change the threshold of the comparator 102b. The output of clamp unit 128 is applied to summing amplifier 133 which provides a threshold to comparator 102b. When this threshold is crossed by the pressure transducer signal on line 123a, comparator unit 102b produces a low pulse on line 103b which is applied to control alarm unit 22, FIG. 10. Failure of this low signal to appear at the end of inhalation produces an apnea alarm indication on panel 12 and also activates an audible alarm. A redundant beeping alarm indicating a machine failure is generated if the output of comparator 102b does not change logic levels at least once every 14 seconds.

2. Time Sensing

The common time reference for the time sensing is a time ramp signal generated by integrator 106 whose rate is adjusted by internal control 105. Following reset, the output of integrator 106 increases from zero at the rate of 333 millivolts per second. The output of integrator 106 is applied to four comparators 104a–d. Each of comparators 104a–d has a voltage threshold input which is a function of front panel control settings and the present operating mode. The time required for the ramp of integrator 106 to reach the applicable one of these thresholds determines the cycling time of the control unit.

The outputs of the comparators on lines 105a–d are applied to the selector unit 16, FIG. 7. Selector unit 16 is effective to select one of the signals on lines 105a–d as commanded by the front panel setting switches. Once a signal has been selected, the selector unit is effective to generate a low pulse on time reset line 125 which drives FET switch 125a (FIG. 6) into conduction and resets integrator 106 by discharging its capacitor.

Inhale time is determined by inspiratory time control 42. The output of the control 42 is applied by way of amplifiers 462 and 463 and electronic switches 129 and 130 to unity-gain buffer amplifiers 464 and 465. Switches 129 and 130 normally connect terminals 129a to 129c and 130a to 130c, respectively. The voltage output of amplifiers 464 and 465 are identical provided inspiratory pause switch 76, panel 12, is off. The outputs of amplifiers 464 and 465 provide the thresholds to comparators 104b–c respectively.

The output of amplifier 464 is applied to comparator 104b and defines tidal volume inhale time which is used in the computation of tidal volume. When integrator output 106 crosses the threshold for comparator 104c it generates a low pulse which is effective to end inspiration if the control is in the inhale mode. The output of comparator 104b is also a low pulse but it is not effective unless inspiratory pause has been selected by switch 76. When inspiratory pause is selected, the output of comparator 104b is the signal which ends inspiration and initiates a pause of duration controlled by front panel control 48. The output of comparator 104c on line 105c which ends the inspiratory cycle when inspiratory pause is not selected, now ends inspiratory pause. This is because the output of inspiratory time control 42 and that of the inspiratory pause control 48 are summed in amplifier 463 and applied by way of switch 130 and the amplifier 465 which thereby changes the threshold for comparator 104c. This threshold voltage is supplied by line 465a to computer unit 18.

The exhale time is controlled by the setting I:E ratio control 40 on the front panel. The control 40 is a variable resistor which sets the gain of amplifier 111 which is effective to amplify the inhale time applied from the output of amplifier 465 by a factor of one to four. The output of amplifier 111 is applied as a threshold to comparator 104d. When the ramp input to comparator 104d exceeds the threshold, a low pulse is generated on line 105d and this pulse is effective to end expiration if the control is in the exhale mode. The output of amplifier 111 is also supplied by way of line 111a to the computer unit 18.

Comparator 104a establishes a safety limit on the respiratory periods. Its threshold is set by internal control 112, which is adjusted to supply 4 volts representing 12 seconds of time. If this threshold is crossed by the output of integrator 106, the output of 104a will develop a low pulse which initiates an inhale if the exhale cycle has not yet ended. This signal is supplied on line 105a to selector unit 16 and thus insures that an inhalation occurs at least every 12 seconds.

During a sigh breath, the signal on line 212a is high and is effective to change the state of electronic switches 129 and 130 so that they connect terminals 129b to 129c and 130b to 130c. Voltage from inspiratory time control 42 is amplified by amplifier 462 to control the inhalation and exhalation times.

IMV timing is established by an integrator 114 which generates a ramp voltage whose rate is set to 333 millivolts per second by a control 113. The output of integrator 114 is applied to a comparator 116 whose other input is obtained from the front panel IMV rate control 36. A low pulse is generated at the output of comparator 116 when the threshold set by control 36 is exceeded by the output of integrator 114. The low pulse output of comparator 116 triggers a one shot 118 which in turn drives a divide-by-ten counter 120 and a FET switch 118a. Conduction of switch 118a is effective to reset integrator 114 to zero by discharging its capacitor. After ten clock pulses, the divide-by-ten counter 120 produces an output on line 120a which is applied to the selector unit 16 and initiates a mandatory breath when the IMV mode is selected.

B. SELECTOR UNIT 16

As shown in FIG. 7, selector unit 16 includes two functional units, viz, a signal selector 460 and a triggered sequencer 461. The primary function of the selector unit is to determine the next mode of operation and then to initiate the execution of that cycle.

Selector gate 110, later described in greater detail, receives signals from sensing unit 14 by way of lines 103d, 105d, 105a, 120a, 105b, 103c, 103a and 105c. Gate 110 also receives signals from switches 60, 75, 73 and 76 on the front panel 12, FIG. 2, by way of lines 60a, 75a, 73a and 76a. The selector gate selects appropriate signals arriving from sensing unit 14 as commanded by the switches. In addition, gate 110 receives inhale, exhale and sigh signals generated by processor unit 20. These signals from processor unit 20 are effective to generate timing changes on lines 110a, 110b, 137a, 137b, and 137c.

The logic of selector gate 110 is such that only one of the signals from sensing unit 14 will meet the conditions set up by the front panel switches and the signals on the processor unit and be passed through. It is this signal which sets the appropriate flip-flop of the group 132a-c by way of gates 139a-c, respectively. The following Table shows the conditions that must be present in order to accept a particular signal from sensing unit 14 and which of flip-flops 132a-c will be set.

TABLE I

| Signal From Sensing Unit 14 | Switches | | | | Mode Being Executed | Sigh | Set Flip-Flops 132a-c (Next Mode of Execute) |
| --- | --- | --- | --- | --- | --- | --- | --- |
| | 60 BPM | 75 Assist | 73 IMV | 76 Pause | | | |
| T-Effort | * | ON | OFF | * | EXH | * | INH |
| TV-Exhend | * | * | OFF | * | EXH | * | INH |
| TV-Safety | * | * | OFF | * | EXH | * | INH |
| IMV Exhend | ON | * | ON | * | EXH | * | INH |
| Inspauzon | * | * | OFF | ON | INH | Not occurring | HOLD |
| TP-Safety | * | * | * | * | INH | occurring | EXH |
| Sigh safety | * | * | OFF | * | INH | occurring | EXH |
| TV Inhend | * | * | OFF | * | INH | * | EXH |

*Condition irrelevent

When one of flip-flops 132a-c is in the set position, the starting gate output 142 changes its logic state and will remain in the state until a reset signal occurs by way of line 140. During this reset cycle, the output of starting gate 142 is applied by way of line 134 and inverter 134a to gates 139a-c to inhibit any additional signals entering the flip-flops. The output of starting gate 142 also resets decade counter 121 to all zeros. When the counter is thus forced out of its end count state, a gate is enabled which allows clock pulses to be counted. Counter 121 sequentially changes state with each consecutive cycle of clock pulses applied by way of lines 160a-b from the clock generator in computer unit 18. The outputs of decade counter 121 are applied to logic gate 122, later described in detail, which generates signals on lines 136, 138, 125 and 140.

The CT 3 signal on line 136 is used to indicate the end of the present mode (inhale, hold, exhale) of operation. The register transfer signal on 138 is supplied to processor unit 20 to effect transfer of the information from the flip-flop. This indicates to the processor unit that a new mode of operation is executed. The timer reset signal on line 125 is applied to sensing unit 14, FIG. 6, to reset the time ramp output of integrator 106. The flip-flop reset signal on line 140 resets the flip-flops 132a-c.

On count 9, the clock pulses to decade counter 121 are inhibited and the counter remains in this state until different modes of operation. The inhale-exhale flip-flop 194 is in the inhale phase during the hold mode.

TABLE II

| COND. | MODE | REG. 190 | REG. 192 | FLIP-FLOP 194 INH | FLIP-FLOP 194 EXH | VALVE STATE 25a | VALVE STATE 25b | VALVE STATE 25c | VALVE STATE 25d |
|---|---|---|---|---|---|---|---|---|---|
| T.V. | INHALE | 1 | 1 | 1 | 0 | 0 | 1 | 1 | 0 |
|  | EXHALE | 0 | 0 | 0 | 1 | 0 | 0 | 0 | 0 |
|  | HOLD | 0 | 1 | 1 | 0 | 0 | 0 | 1 | 0 |
|  | EXHALE + PEEP | 0 | 0 | 0 | 1 | 0 | 0 | 0 | 1 |
| IMV | INHALE | 1 | 1 | 1 | 0 | 0 | 1 | 1 | 0 |
|  | EXHALE | 0 | 0 | 0 | 1 | 1 | 0 | 0 | 0 |
|  | EXHALE + PEEP | 0 | 0 | 0 | 1 | 1 | 0 | 0 | 1 |

Legend
Valves 25a,b
1 - valve open (energized)
0 - valve closed (deenergized)
Valves 25c,b
1 - valve input open to output, exhaust closed (energized)
0 - valve output open to exhaust, input closed (deenergized)

another signal is selected by gate 110 and flip-flops 132a–c change state and the above sequence repeats. The power initialization signal on line 220a is obtained from control alarm unit 22, FIG. 10. The signal on line 220a sets decade counter 121 to a count of nine and timer and flip-flop reset pulses are generated by logic gate 122. This sets up a condition as if a mode transfer had occurred.

C. PROCESSOR UNIT 20

Figure 9:
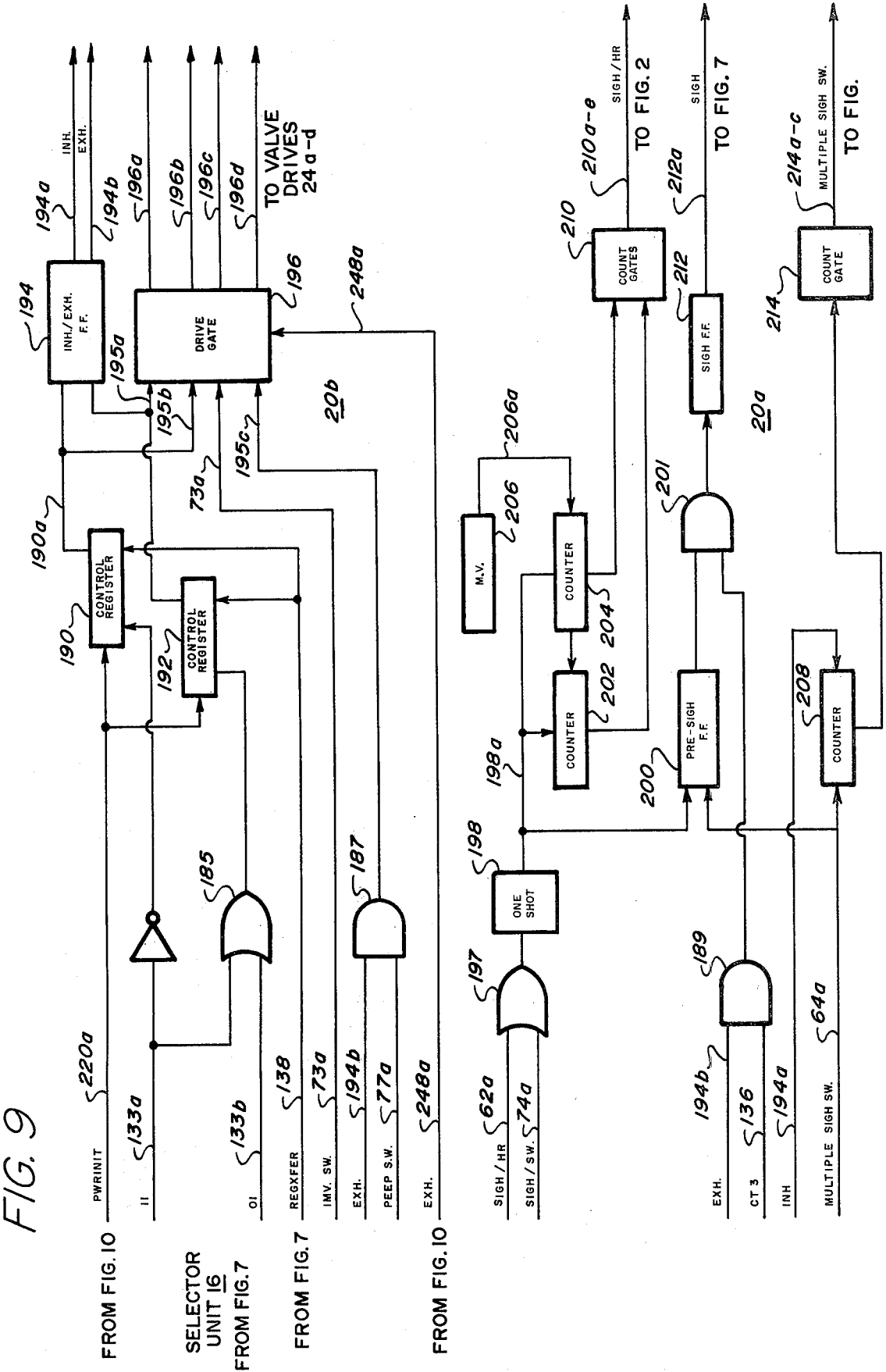
FIG. 9 illustrates in more detail and in block diagram form the processor unit of FIGS. 5A-B.

Processor unit 20 shown in FIG. 9 is effective to produce control signals to drive solenoid valves 25a–d in the control unit pneumatics shown in FIG. 4, and thus determines the mode of ventilator operation. Unit 20 also causes the occurrence of sigh breaths at a frequency and in multiples corresponding to the setting of the sigh controls 62, 64 on front panel 12.

The outputs of inhale and hold flip-flops 132a, 132b of selector unit 16 (FIG. 7) are applied by way of lines 133a and 133b to control registers 190 and 192 of unit 20. However, the data from the flip-flops 132a, 132b is not stored in these registers until the register transfer pulse on line 138 is obtained from selector unit 16. It is at this time that the output of the D type control flip-flops 190 and 192 are decoded to effect one of the three phases of operation, viz, inhale, hold and exhale. These signals are applied to inhale, exhale flip-flop 194 and to drive gate 196, later described in greater detail. It should be understood that control registers 190 and 192 are initialized by power initialization signal on line 220a obtained from control alarm unit 22. This will ensure the proper sequence of operation during the power switching mode.

The outputs of control registers 190 and 192 set and reset flip-flop 194 to generate an inhale signal on line 194a and an exhale signal on 194b. By way of drive gate 196 and the amplifier in valve drive unit 24, the control registers also drive volume mode solenoid 25b to control the main flow to the patient and drive airway valve solenoid 25c. The IMV valve drive signal on line 196a is generated by control register 192 and the IMV switch signal from front panel 73 by way of line 73a. The PEEP drive on line 196d is generated by combination of the output 194b of flip-flop 194 and the logic level from PEEP switch 77 by way of line 77a. The exhaust signal on line 248a is obtained from control alarm unit 22 which is applied to drive gate 196 and is effective to deenergize solenoid valves 25b–d which when switched to relieve the breathing circuit pressure. Table II shows the output logic level of the control registers, inhale-exhale flip-flop and solenoid valve drive signals during The sigh control portion of processor unit 20 as shown in FIG. 9 is the other function of this unit. The sigh rate is generated by an astable multivibrator 206 whose output by way of line 206a is applied to counters 204 and 202. A pulse is developed every ten seconds by the multivibrator 206. The output of counters 202 and 204 are gated by means of count gates 210 to produce outputs on line 210a which occur at various multiples of ten seconds following counter reset. These count outputs represent 24, 30, 36, 45, 60 and 90 counts and are supplied by lines 210a–e to various contacts of front panel switch 62. One of these count outputs is selected by switch 62 and applied by way of line 62a to OR gate 197. The other input to the gate 197 is obtained from the sigh switch 74 on panel 12 which enables gate 197 when switch 74 is on. When the selection count pulse appears, the output of gate 197 is applied to a one shot 198 whose output by way of line 198a is effective to set the pre-sigh flip-flop 200 and reset decade counters 202 and 204 in order to start a new timing cycle. These conditions will also occur when sigh switch is initially depressed to immediately produce a sigh breath on manual command.

The sigh signal on line 212a does not occur until sigh flip-flop 212 is set. The conditions to set this flip-flop 212 include the pre-sigh flip-flop set and the end-of-exhale generated by the combined presence of exhale signal 194b and the count-three signal 136. At this point, a sigh breath will occur on the next inhale. The number of consecutive sigh breaths to be delivered is determined by a decade counter 208 whose output is decoded by gate 214 and applied by way of lines 214a–c to the multiple sigh switch 64. The clock pulses for the counter are produced when a sigh inhale is requested by way of line 194a. When the proper count output is present, pre-sigh flip-flop 200 and multiple sigh counter 208 are reset by way of line 64a. Sigh flip-flop 212 is not reset until the last sigh breath is completed. A power initialization signal resets all flip-flops and decade counters.

D. CONTROLLER PNEUMATIC UNIT

The pneumatic system of control unit 10 is shown schematically in FIG. 11 which represents in more detail the system shown by the block diagram in FIG. 4. Drive gate 196 of the processor unit 20, FIG. 9, drives solenoid valves 25a–d. Air-oxygen mixture is supplied by line 37b from the air-oxygen mixer unit 37 of the console unit to the filter 350 and pressure switch 352.

When activated, the pressure switch provides a signal to NOR gate 241 in control alarm unit 22, FIG. 10, and produces an audible and visual alarm. The output of the pressure switch 352 is applied to regulator 354 which holds the output pressure within the range of 33 to 38 PSIG for maintaining calibrated output flow. The output of regulator 354 is supplied to the IMV mode solenoid valve 25a, the volume mode solenoid valve 25b and the regulator 356.

Under normal volume mode of operation, valve 25b is open and the valve 25a is closed. The output of the volume solenoid valve is applied through orifice 44a to a pneumatic flow control 44 located on pneumatic chassis. The output of the flow control 44 is applied by way of airway manifold 381 to the front panel airway outlet 98. Valves 380, 382 limit pressures reaching patient circuit 32.

In the IMV mode of operation, valve solenoid 25a is energized with simultaneous deenergizing of valve solenoid 25b. In this mode, the output of regulator 354 is applied through solenoid 25a and controlled by IMV flow control 38 and then passed through the airway manifold 381 and onto the front panel airway fitting 98.

Airway pressure is measured by way of a line connected to fitting 100 on front panel 12 of control unit 10 and applied to a pressure gauge 84 and a pressure sensing manifold 375. Gauge 84 is a mechanical unit and is independent of any electrical power supply applied to the control unit. Thus, this gauge is still active even under power failure. Manifold 375 contains a baffle 376 to dampen any oscillations of pressure before it is applied to transducer 15. The transducer output is used by sensing unit 14 as shown in FIG. 6 to compare with front panel settings and generate independent control signals as previously described. Manifold 375 and gauge 84 are coupled by way of a 0.2 liter-per-minute orifice 84a which is supplied with air by way of volume mode solenoid 25b. The initial flow of dry gas insures that no moisture enters the pressure sensing transducer and its associated connections, from the inspiratory patient circuit.

Volume mode solenoid 25b also supplies gas to the nebulizer switch 92 which is a manually operated valve located on panel 12. When the nebulizer switch is on, the output gas flows through restrictive orifice 92b to nebulizer outlet 94. When off, the gas flows through orifice 92a to manifold 381. Orifices 92a and 92b are sized so that a flow of approximately 8 liters-per-minute to the nebulizer matches exactly the flow to the airway manifold. Nebulizer switch 92 is controlled by the panel mounted switch handle shown in FIG. 2.

The output of regulator 354 is applied to regulator 356 which regulates the output pressure to 2-3 PSIG and supplies gas to solenoid 25c. When energized, valve 25c supplies gas flow to fitting 96. Outlet 96 is applied by way of a flexible tubing 96a to airway valve 13 and IMV valve 17 as shown in FIG. 1. The exhaust port of airway valve 25c is connected to the output of valve 25d when 25c is deenergized.

PEEP solenoid valve 25d supplies gas flow, when energized, to the output of PEEP regulator 50 which is self-relieving and maintains adjustable output pressure in the entire circuit connected to the patient's airway valve. Regulator 50 is controlled by way of a knob 50a shown in FIG. 2. The exhaust port of valve 25d is vented to ambient atmospheric pressure when valve 25d is deenergized. Therefore, the patient airway valve is exhausted to ambient atmosphere when valves 25c and 25d are deenergized. When valve 25c is deenergized and valve 25d is energized, the patient airway valve is exhausted to the PEEP regulator at a positive pressure which is adjustable as described above.

Table III shows the function of solenoid valves 25a-d with different functional modes of operation for the volume ventilator.

TABLE III

| Function | Phase | VALVE STATE | | | |
|---|---|---|---|---|---|
| | | 25a | 25b | 25c | 25d |
| Volume | inhale | 0 | 1 | 1 | 0 |
| | exhale | 0 | 0 | 0 | 0 |
| IMV (Mandatory breath) | inhale | 0 | 1 | 1 | 0 |
| | exhale | 1 | 0 | 0 | 0 |
| IMV (Intermittent breath | inhale | 1 | 0 | 0 | 0 |
| | exhale | 1 | 0 | 0 | 0 |
| Sigh | inhale | 0 | 1 | 1 | 0 |
| | exhale | 0 | 0 | 0 | 0 |
| Assist | inhale | 0 | 1 | 1 | 0 |
| | exhale | 0 | 0 | 0 | 0 |
| Inhalation Plateau | inhale | 0 | 1 | 1 | 0 |
| | hold | 0 | 0 | 1 | 0 |
| | exhale | 0 | 0 | 0 | 0 |
| Volume + PEEP | inhale | 0 | 1 | 1 | 0 |
| | exhale | 0 | 0 | 0 | 1 |
| IMV + (Mandatory PEEP breath) | inhale | 0 | 1 | 1 | 0 |
| | exhale | 1 | 0 | 0 | 1 |
| IMV + (Intermittent PEEP breath) | inhale | 1 | 0 | 0 | 1 |
| | exhale | 1 | 0 | 0 | 1 |

See Legend in Table II.

E. COMPUTER UNIT 18

Figure 8:
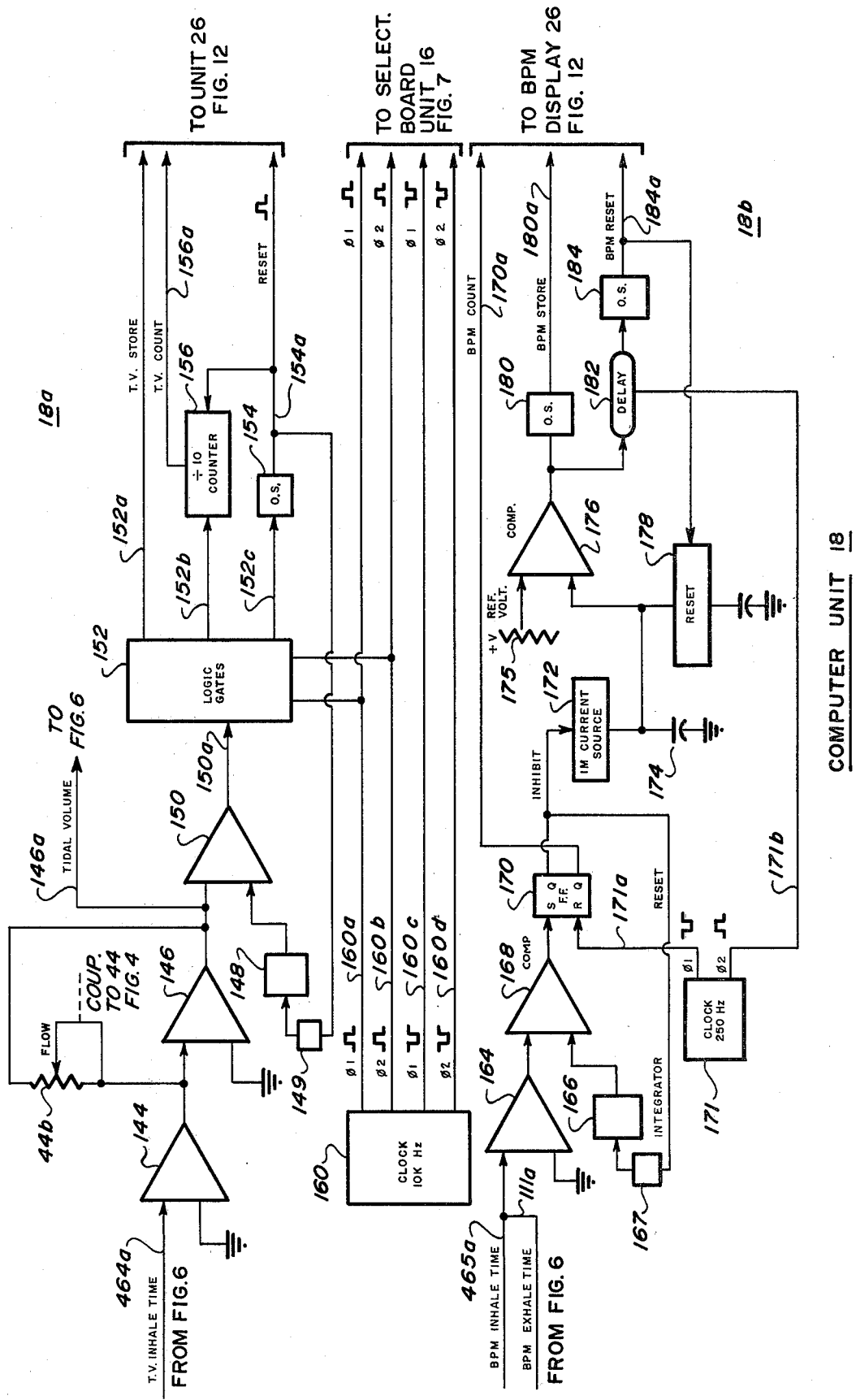
FIG. 8 illustrates in more detail and in block diagram form the computer unit of FIGS. 5A-B.

Computer unit 18 shown in FIG. 8 computes the tidal volume and breaths per minute from analog signals received from sensing unit 14 and conveys this information in digital form to display unit 26 for display on panel 12.

The tidal volume is computed by multiplying the inhalation time supplied on line 464a with the flow rate signal generated by a potentiometer 44b mechanically coupled to flow control 44 as shown in FIG. 8. The signal on line 464a is amplified by amplifier 144 and then coupled to the input of an operational amplifier 146. The gain of amplifier 146 is controlled by the resistance of flow control potentiometer 44b. The setting of potentiometer 44b is directly proportional to the calibrated flow control settings between 0.2 and 2.0 liters per minute. The output of amplifier 146 on line 146a is proportional to the product of the inhalation time signal and the gas flow rate, and thus to the tidal volume. The voltage on line 146a is supplied to sensing unit 14 in FIG. 6 to determine the apnea threshold as previously described.

The output of amplifier 146 also applied to a comparator 150 which is supplied with another signal from an integrator 148 which is effective to generate a ramp at the rate of 0.1 volt per millisecond following reset to zero. The time it takes for integrator 148 to reach the threshold established by 146 is a conversion period. It is this time period that determines the number of counts conveyed to display unit 26 by way of line 156a. The output of comparator 150 is applied to logic gates 152, later described in detail, under the control of clock pulses supplied by clock generator 160 on lines 160a and 160b. At the end of a conversion period, the output of comparator 150 changes state and the counts to the display unit 26 are disabled. When the next clock pulse appears on line 160b, the number of counts stored in counters 274, 276, 278 (FIG. 12) of display unit 26 are transferred to front panel display 82a-c under the control of TV store line 152a.

When the next pulse appears on line 160a, a one-shot 154 resets decade counter 156 and resets decade counters 274, 276, 278, FIGS. 8,12, by way of line 154a. Line 154a is also effective to reset integrator 148 by causing FET switch 149 to discharge its capacitor. When integrator 148 is reset, comparator output 150 returns to its normal state. This once again enables the count pulses and a new conversion cycle takes place. It should be understood that decade counter 156 is effective to reduce the number of count pulses applied to display unit 26 by a factor of ten and thereby eliminates variation that would otherwise be observed on the least significant digit.

BPM is calculated by dividing the number sixty by the (inhalation+exhalation) time in seconds represented by signals on lines 111a and 465a as shown in FIG. 8. The signals on lines 111a and 456a are received from sensing unit 14 and applied to a summation amplifier 164. The output of amplifier 164 is applied to a comparator 168. The other input to the comparator is generated by an integrator 166 which provides a signal that increases at a rate of 3.33 volts per millisecond following each reset to zero. During the period of time that integrator 166 is integrating to the threshold set by amplifier 164, one milliampere from current source 172 charges capacitor 174. When integrator 166 crosses the threshold set by amplifier 164 comparator 168 sets flip-flop 170.

The output of flip-flop 170 on line 170a is applied to decade counters 270, 272 (FIG. 12) in display unit 26. When flip-flop 170 is set current source 172 is inhibited from further charging capacitor 174. The voltage level on capacitor 174 at this time is dependent upon the time it took integrator 166 to integrate to its threshold voltage. The capacitor 174 will hold this charge until a low frequency clock pulse from clock generator 171 on line 171a resets flip-flop 170. At this time, integrator 166 is reset by FET switch 167 which discharges the integration capacitor, after which it will again start to integrate and current source 172 will continue to charge capacitor 174. The circuit will continue in this mode of operation until the charge on capacitor 174 reaches the referenced voltage set up by potentiometer 175.

The output voltage on capacitor 174 resembles a staircase and the number of steps it must take to reach the reference voltage is dependent upon the amount of charge current source 172 can deliver between consecutive pulses on line 171a. These steps correspond to the number of count pulses sent out on line 170a and thus to the number of breaths per minute. The voltage of capacitor 174 and the reference voltage 175 are applied to a comparator 176. When the capacitor voltage reaches the reference voltage the output of comparator 176 changes state and triggers a one-shot 180 which is effective to generate a store signal on line 180a which transfers the number stored in counters 270, 272 to displays 80a, 80b, FIG. 12. The computed breaths per minute is thus displayed numerically. The output of comparator 176 also enables a delay circuit 182, and allows a clock pulse on line 171b to trigger one-shot 184. The output of one-shot 184 on line 184a resets decade counters 270, 272 and also discharges capacitor 174 by way of reset circuit 178. When capacitor 174 discharges to zero, the output of comparator 176 returns to its normal state and a new conversion takes place.

F. DISPLAY UNIT 26

As shown in FIG. 12, display unit 26 comprises decade counters and numeric display modules. The display unit is divided into two functional entities or sections, viz, the breath-per-minute display section 26b and tidal volume display section 26a. BPM display 26b has two decade counters 270 and 272 and numeric display modules 80a,b. The decade counters are cascaded so that, following the reset pulse on line 184a, decade counter 270 will continuously change states sequentially from 0 to 9. At state 9, the following pulse causes the counter 270 to change from 9 back to 0 and at the same time outputs a carry pulse which is applied to decade counter 272. Counter 272 then advances its states in the same manner but only once for every ten counts made by counter 270. Thus, the two decade counters in combination can count and store any number of pulses ranging from 0 to 99.

The output of each counter appears on four lines in a BCD code so that each combination of highs and lows on the four lines uniquely represents a digit between 0 and 9. This code is recognized by display module 80 so that when it receives a store pulse on line 180a, the module displays the numeral corresponding to the code then present. This numeral remains displayed until the next time a store pulse appears on line 180a.

In the display cycle, following the signal on reset line 184a, a number of pulses appear on count line 170a as was set forth in the foregoing description of computer unit 18. Thus, the number of pulses delivered to the decade counter corresponds to the number of breaths per minute computed. After the last such pulse appears on the count line, a store pulse appears on line 180a which will cause the numeric displays 80 and 82 to store the code and display the numerals corresponding to the code. Thus the computed number of breaths per minute is displayed so that the operator can read this information. A reset pulse appears on line 184a following the store pulse, and resets the counters to their zero states, after which the display cycle repeats.

Tidal volume section 26a operated works in exactly the same way as described above except that three decade counters 274, 276, 278 are cascaded and drive three display modules 82a-c respectively. Thus, a number of counts ranging from 0 to 999 can be counted and then stored for display.

G. CONTROL ALARM UNIT—22

Control alarm unit 22 shown in FIG. 10 monitors pressure or internal failures and indicates which alarm condition is activated by visual and/or audible means. A pressure failure is indicated by a continued audible alarm whereas an intermittent (beeping) tone is indicative of an internal failure. A visual indication of apnea or pressure failures is displayed by an appropriate flashing light on the front panel.

The apnea alarm is activated when (1) a high logic level is present on line 103b of sensing unit 14, FIG. 6, (2) there is an inhale mode signal on line 194a and (3) there is also a CT 3 pulse on line 136. When these conditions are satisfied, an apnea flip-flop 238 is set and audible alarm 250 and visual alarm lamp 86 are turned on. Each alarm is reset when the signal on line 103b is low and inhale signal 194a and CT 3 signal 136 are present.

The pressure alarm may be turned on either by pressure switch 352, FIG. 4, opening and producing a signal on line 68a or exceeding of the pressure limit control as indicated by a signal on line 110b. If the supply pressure drops to 20 PSIG or less, pressure switch 352 opens causing pressure alarm lamp 88 and audio alarm 250 to turn on continuously until the supply pressure is regained and the switch closes.

If either the sigh or normal pressure limits 54, 52 respectively are exceeded, a pulse is generated by selector unit 16, FIG. 7, on line 110b. This exhaust request pulse triggers a one-shot 248 whose duration is 2 seconds. The output of this one shot turns on pressure alarm lamp 88 and audible alarm 250 and also develops an exhaust signal on line 248a which opens the patient valve by way of the processor unit 20, FIG. 9. It is in this way that the pressure to the patient is released. Both the apnea and pressure alarms can be tested by pushing a front panel switch 90 and activating line 90a. When depressed, a high logic level is generated on line 90a which turns on the alarm drivers until the test switch is released.

The beeping alarm is caused by a missing pulse detection or a voltage monitor signal indicative of a power failure. The triggering of missing pulse detector 236 is done by monitoring the output of apnea comparator 102b on line 103b, FIG. 6. The signal on line 103b is applied through a threshold crossing detector 234 which drives missing pulse detector 236. If the missing pulse detector is not triggered in 14 seconds, a high pulse is produced which turns on audio beeper 240. A voltage monitor 232 monitors +5, +12, −12 volt power supplies by comparing the voltages on these buses against independently derived reference voltages in, for example, a set of comparators. One or more comparators would generate a high logic state when any of the regulated voltages drift outside of their set limits. This is also effective to turn on beeping alarm 240. In case of a power failure, storage capacitor 250a for alarm 250 is effective to produce an audible signal for approximately 1 minute. Also contained in control alarm unit 22 is an assist flip-flop 222 which is set by a pulse on line 110a from selector unit 16, FIG. 7, and is reset by the pulse on line 105d from sensing unit 14, FIG. 6. The pulse on line 110a occurs if assist switch 75 is on and the patient makes an effort to inhale such that the airway pressure sensed by pressure transducer 15 exceeds the assist pressure threshold set by control 46. This produces an inhalation time which differs from that set by the controls and thereby cause the actual breaths per minute to depart from the value displayed on BPM indicator 80. To alert the operator to this fact, flip-flop 222 when set by such a pulse enables NAND gate 223 whose other input is supplied by a free running multivibrator 226 having a cycling rate of two times per second. The output of gate 223 is applied to BPM driver 224 which supplies the BPM blink signal on line 224a to the display unit 26, FIG. 12.

Assist flip-flop 222 is reset by a pulse on line 105d from sensing unit 14 which occurs at the end of the exhale period. Thus, whenever the assist mode is selected, any breathing effort made by a patient that causes pressure changes above the set threshold will cause the BPM numeric display to periodically blink off about at the rate of once every half second to alert the operator to the fact that the otherwise displayed breaths per minute is being altered by such effort. At the end of exhalation for that particular breath the BPM display is once again illuminated steadily. In all other modes flip-flop 222 cannot be set and the BPM display will always be continuously illuminated and will not blink.

Pulses from multivibrator 226 are supplied to divide-by-ten counter 228 whose output is amplified by driver 230. This output, causes audible alarm 250 to pulse briefly every five seconds when switch 231 is not set to engage the output of alarm driver 242.

A power initialization signal is generated on line 220a by unit 220 when ventilator power is turned on and also when the manual power switch 71 is depressed. The purpose of this signal is to set the ventilator to the inhale phase.

H. CONSOLE ALARM UNIT—28

Figure 14:
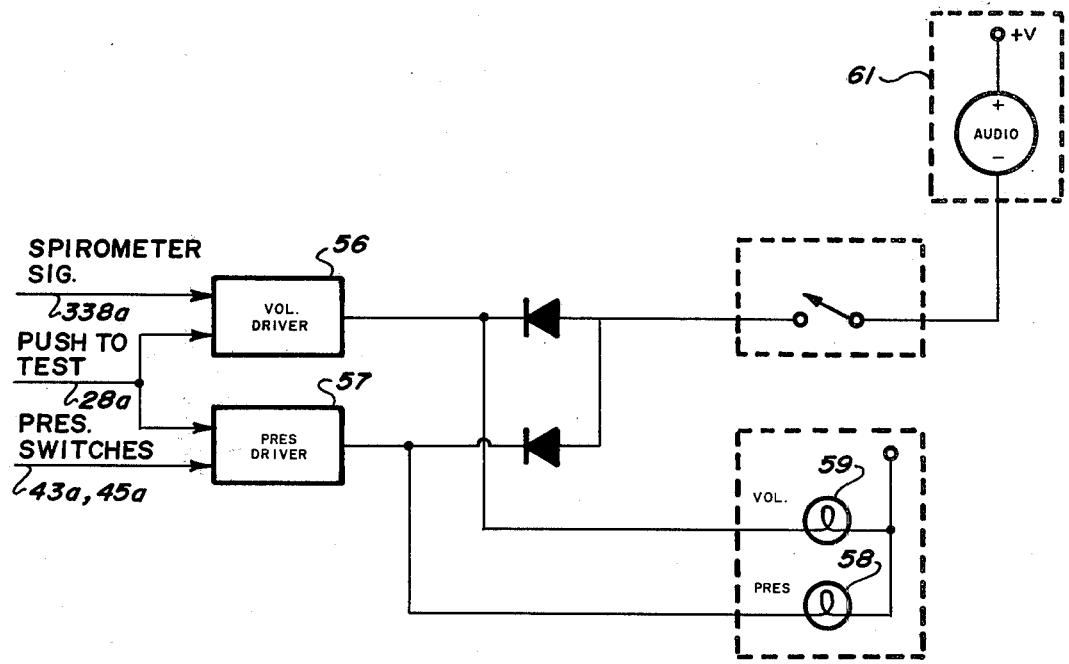
FIG. 14 illustrates in more detail and in block diagram form the console alarm unit of FIGS. 5A-B.
Figure 17:
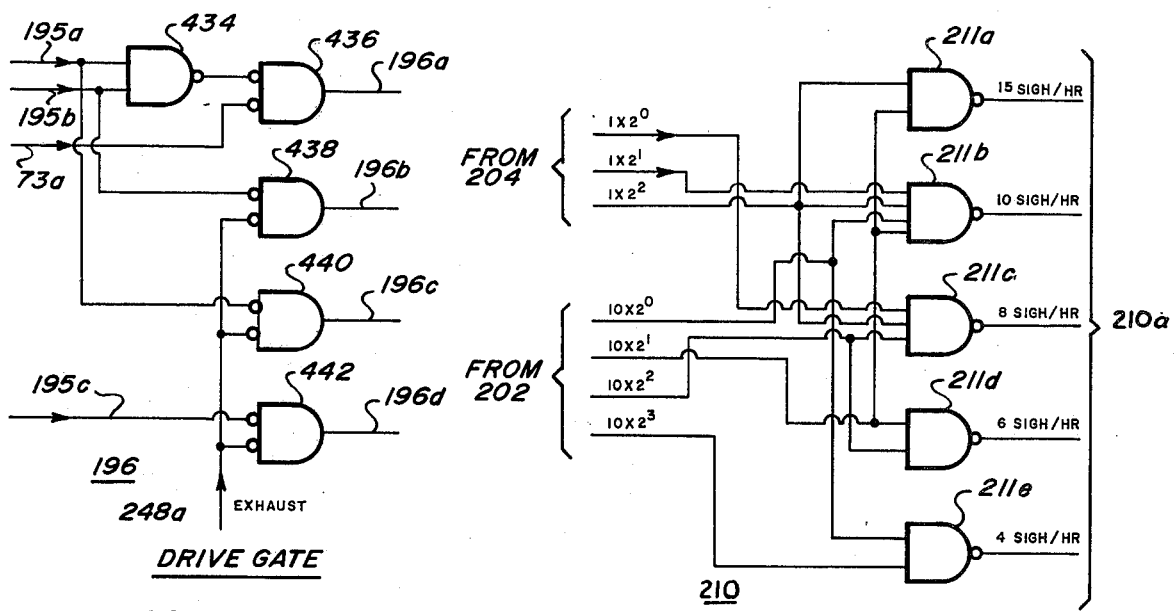
FIG. 17 illustrates the detailed block diagram of the drive gate of the processor unit of FIG. 9.
Figure 18:
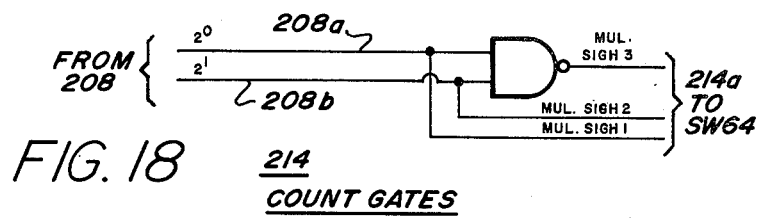
FIG. 18 illustrates the detailed block diagram of the count gates of the processor unit of FIG. 9.

Console alarm unit 28 shown in FIG. 14 generates alarm signals in response to low air or oxygen pressure and low minute volume sensed by spiromater 15. The volume alarm receives a signal on line 338a when the minute volume reading exceeds either a high or low limit setting. The signal on line 338a is effective to turn on volume driver 56 to cause audible alarm 61 to sound and turn on volume alarm indicator lamp 59. The pressure alarm is initiated by low air pressure or oxygen pressure which activates switches 43 and 45 to generate a signal on line 43a, 45a. These signals are applied to driver 57 which is effective to turn on the audible alarm 61 and also turn on alarm indicator lamp 58. The push-to-test switch 28a is effective to drive both 56 and 57 thus providing an audible alarm and lighting lamps 58 and 59.

I. SPIROMETER PROCESSOR 33

Spirometer processor 33 shown in FIG. 15 is used for processing the output of spirometer flow sensor 30 disposed in patient circuit 32, FIG. 1. Spirometer 30 is a miniature turbine which is rotated by gas flowing past its blades. Each revolution of the turbine produces an output pulse. The output signal from sensor 30 is amplified by amplifier 324 which drives pulse shaper 326. The rectangular wave shape output of the pulse shaper is then used to trigger a monostable multivibrator 328 and a gating circuit 330. One-shot 328 produces a constant width pulse with each pulse from 326. These pulses turn on a transistor switch 332 which connects a positive voltage to a series RC circuit comprising a variable resistor 340 and capacitor 335. It will be understood that switches 331, 333 and 337 can be positioned either in the tidal volume or minute volume modes. In the tidal volume mode the switch arms are in positions 331a, 333a and 337a respectively whereas they are in positions 331b, 333b and 337b in the minute volume mode.

In the tidal volume mode, the resultant charge on capacitor 335 is proportional to the internally set pulse width and the number of pulses produced during the expiration cycle. The voltage on capacitor 335 is applied to buffer amplifier 336 whose output is applied to meter 33a, FIG. 1. In parallel with the monostable circuit 328, a gating circuit 330 receives pulses from pulse shaper 326. As the flow through the transducer decreases, the time period between the output pulses starts to increase. It will continue to increase until it reaches a predetermined time set internally with the gating circuit. At that point, the gating circuit will turn on FET 334 which shorts capacitor 335 to ground and the meter deflects back to zero. This features eliminates any indication of readings below the range of interest.

In the minute volume mode switches 331 and 333, 337 are in position 331b, 333b and 337b respectively. In this position, FET switch 334 is no longer in the circuit and capacitor 335 is charged by resistor 341 and discharged through resistor 342. Capacitor 339 is now introduced in the feedback circuit for amplifier 336. This capacitor 339 is effective to produce a time delay which is of sufficient duration so that between expirations, capacitor 335 fully discharges the output of amplifier 336 but it remains at some DC level. Eventually, the output of 336 will reach the peak value of capacitor 335 thus the meter 33a indicates the minute volume.

The minute volume alarm is activated by comparing an upper and lower limit set up by potentiometers 340 and 342 in a dual comparator 338. If either threshold is crossed, the comparator switches and produces a signal on line 338a which is applied to the console alarm unit 28 shown in FIG. 14 which is effective to produce an audible and visual alarm as previously described.

IV. DETAILED EXPLANATION OF GATES

A. LOGIC GATES 122—FIG. 13

As previously described in FIG. 7, decade counter 121 provides input signals to logic gates 122. When decade counter has counted nine pulses, further counts are inhibited and it remains in this state. Decade counter 121 is reset by line 142a and is thereby enabled to count clock pulses appearing on lines 160a–b. Thus line $2^0$ provides a pulse for every two input pulses on lines 160a–b. In conventional manner for every two pulses on line $2^0$ there is produced one pulse on line $2^1$; for every four pulses on line $2^0$ there is one pulse on line $2^2$; and for every ten pulses on line $2^0$ there is one pulse on line $2^3$.

The signal on line $2^0$ is inverted and applied to one input of a NAND gate 390. The other input to this gate is from line $2^3$. Line $2^0$ is also applied to AND gate 392 which has its other inputs coming from lines $2^1$ and $2^2$. The output of AND gate 392 is applied to AND gate 394, the other input of which is obtained from output 133b of hold flip-flop 132b. Accordingly, gate 394 produces a pulse at CT 3 output 136 which occurs three clock periods after counter 120 is enabled.

Line $2^2$ from counter 120 is also applied to one input of AND gate 396 with the other input applied from a NAND gate 398. The inputs to gate 398 are from output 73a of IMV switch 73 and from exhale line 194b of flip-flop 194 of unit 20, FIG. 9. The remaining input to gate 396 is the power interrupt input 220a. Accordingly, gate 396 produces an output signal occurring during the fourth through seventh clock periods following enablement of counter 121 when flip-flop 194 goes to its exhale state and with IMV switch 73 in its on position. In addition, gate 396 produces a signal on timer reset line 125 when power is first turned on for the ventilator system. The timer reset signal on line 125 is effective to reset the time base of integrator 106 of sensing unit 14 of FIG. 6 by way of switch 129.

The output of gate 390 is applied to one input of a NOR gate 402, the other input of which is coupled to a clock line 160c. Output 138 is applied to registers 190, 192 in unit 20 of FIG. 9. Accordingly, gate 402 produces a short pulse during the eighth clock period and register counter 121 is enabled. In this manner, there is an effective transfer of flip-flop states.

The output of gate 390 is also applied to gate 404 having as its other input clock line 160d. The output of gate 404 is applied to NOR gate 406 which produces an output on line 140 which occurs just after the pulse on line 138. The purpose of the pulse on line 140 is to reset flip-flops 132a–c.

B. SELECTOR GATES 110—FIG. 16

In FIG. 7, gates 110 accept status signals from switch panel 12, FIG. 2 and also compares the outputs from sensing unit 14 of FIG. 6. In addition gates 110 accept the status signal from flip-flop 194, FIG. 9 and sigh flip-flop 212. An appropriate combination of the foregoing signals is used to set flip-flops 132a–c and also provides signals on 110a–b.

Specifically, T-EFFORT-P line 110a is provided with a signal from a NAND gate 408 when assist switch 75 is on and when a transition occurs on T-EFFORT line 103d. Line 103d is coupled to comparator 102d of sensing unit 14, FIG. 6.

TP SAFETY line 103c is connected to a NOR gate 410, the other input of which is coupled to sigh line 212a from unit 20, FIG. 9. Line 212a is also coupled to one input of a NOR gate 412. The other input to gate 412 is coupled to sigh safety limit line 103a, FIG. 6. Gates 410 and 412 are coupled through a NOR gate 414 which provides a signal on line 110b and one input to a NAND gate 416. A signal is produced on line 110b for either of the following conditions. In the first of the conditions, line 103c provides a low signal and sigh flip-flop 212, FIG. 9 is set. In the other condition, line 103a provides a low signal and sigh flip-flop 212 is cleared.

T.V. INHEND line 105c from FIG. 6 and inhale line 194a from FIG. 9 are applied through an AND gate 418 to the other input of gate 416. Accordingly, when line 105c provides a signal and inhale/exhale flip-flop 194 is in its inhale state, then gate 416 is enabled. Thus if there is no signal on line 110b there is produced an output signal on line 137c which is effective to set exhale flip-flop 132c when gate 139c is enabled.

Gate 420 is effective to produce an output when IMV switch 73 is on, pause switch 76 is on, and there is a transition of the signal on INSPAUZON line 105b which is coupled through differentiator 419 to gate 420. Line 105b is taken as an output from comparator 104b of sensing unit 14, FIG. 6. The output of gate 420 is applied to AND gate 422 which produces a signal on line 137b when flip-flop 194 is in the inhale state and flip-flop 212 is set.

AND gate 424 provides an output signal when IMV switch 173 is on, IMV switch 60 is on, and the signal on IMV EXHEND line 120a has a transition which is coupled through differentiator 423 to gate 424. The signal on the output of gate 124 is applied through OR gate 430 and then through AND gate 432 when flip-flop 194 is in its exhale state. Accordingly, there is produced a signal on line 137a, thereby to set inhale flip-flop 132a when gate 139 is enabled. Further, the other input to OR gate 430 is from AND gate 428, having one input coupled to gate 426. Gate 426 provides an output signal when either of lines 105a, d are active or an output is produced on line 110a, as previously described. Accordingly, with an output from gate 426, gate 428 produces an output signal when IMV switch 73 is off.

C. DRIVE GATE 196—FIG. 17

For the purpose of this explanation, it will be understood that a high on any one of lines 196a–d, FIG. 9 is effective through a respective driver 24a–d of unit 24, FIG. 4 to energize a respective solenoid valve 25a–d, FIGS. 4, 5. Lines 195a,b are applied to a NAND gate 434, the output of which is applied to one input of NOR gate 436 having an output 196a. Lines 195a,b are also applied to inputs of gates 438, 440 with the remaining inputs to these gates coming from exhaust line 248a, FIG. 10.

A high on lines 195a,b produces a low from gate 434 which in turn produces a high on line 196a if IMV switch 73 is on. In this manner, IMV flow solenoid 25a is actuated. Further, if exhaust line 248a is low and line 195b is low, then a high is produced on line 196b thereby to energize main flow solenoid 25b.

Similarly, with line 195b low and line 248a being low, then line 196c is high therby to energize airway valve solenoid 25c. Line 195c is a low when both exhale line 194b is high and PEEP switch 77 is on. With line 195c being low and line 248 being low, line 196d is high thereby to energize PEEP valve 25d.

It will be seen that exhaust line 248a is provided by one shot 248, FIG. 10 which is actuated by exhaust request line 110b and is provided by selector gates 110 of selector unit 16, FIG. 7.

D. COUNT GATES 210, 214—FIG. 18

Counters 204 and 202 in FIG. 9 provide three and four inputs, respectively, to a series of NAND gates 211a-e. The five outputs of these gates are coupled to a sigh-per-hour selector switch 62 on FIG. 2 which selects one of the five output lines. As shown in FIG. 9, the selected output line is coupled back by way of line 62a through gate 197 to one shot 198 and line 198a thereby to reset counters 202, 204. For example, if the 15 sigh-per-hour output of gate 211a is selected then an output will be produced twenty-four ten-second periods after counters 202, 204 are reset. This output resets counters 202 and 204 as explained above. In this manner the counters 202, 204 recycle every twenty-four ten second periods, thus providing the fifteen sighs per hour rate. The remaining output lines 210b-e operate similarly.

As shown in FIG. 9, counter 208 changes state and responds to signals on line 194a. The output of counter 208 is applied by way of two lines 208a-b ($2^0$ and $2^1$) to counter gate or AND gate 214. It will be seen that multiple sigh 1 line is coupled to the $2^0$ line 208a and multiple sigh 2 line is coupled to the $2^1$ line 208b. Multiple sigh 3 line is the output of AND gate 214. Lines 214a are coupled to multiple sigh switch 64, FIG. 2, which switch is effective to select one of the three sigh lines. The output of switch 64 then feeds back by way of line 64a to counter 208.

Accordingly, if multiple sigh 1 line from gate 214 is selected by switch 64, then counter 208 is reset after one pulse appears on line 194a. If multiple sigh 2 line is selected, then two pulses appear on line 194a and if multiple sigh 3 line is selected then three pulses appear on line 194a. In this manner, there is generated depending on the setting of switch 64, one sigh breath, two sigh breaths, one after the other; or three sigh breaths one after the other.

E. LOGIC GATES 152-FIG. 19

Figure 19:
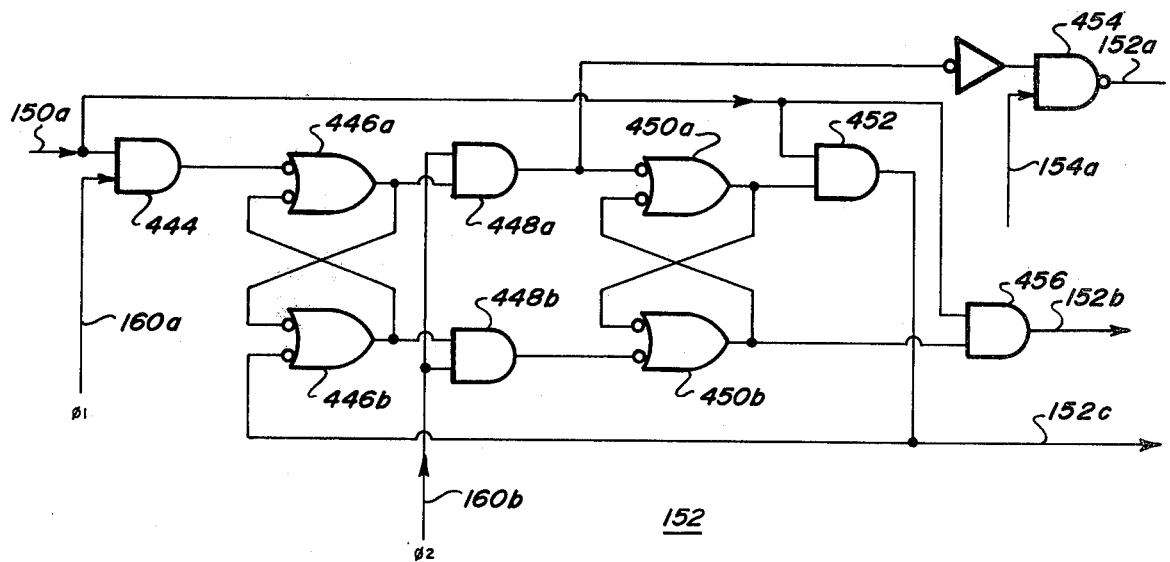
FIG. 19 illustrates the detailed block diagram of the logic gates of the computer unit of FIG. 8.

In FIG. 8, the signal on line 150a is high for a time period which is proportional to the computed tidal volume. This high signal on line 150a enables NAND gate 444 in FIG. 19. The other input to gate 444 is a 10 KHz clock signal on $\phi 1$ line 160a. A first clock pulse is effective through gate 444 to set flip-flop 446a-b which is then effective to enable NAND gate 448a. The output of gate 448a sets flip-flop 450a-b when line 160b provides a second $\phi 2$ clock pulse from clock 160.

The output of flip-flop 450a-b enables gate 456 which provides a series of pulses by way of line 152b to decade counter 156, FIG. 8. At the end of the clock pulse on line 160b, flip-flop 450a-b is reset. In this manner a series of pulses appears on line 152b at a 10 KHz. rate for as long as the signal on line 150a is high. Accordingly, the number of pulses on line 152b is related to the computed tidal volume. When line 15a goes low, a reset signal is generated on line 152c thereby to reset flip-flop 446a-b, integrator 148, FIG. 8 and the counters in unit 26. An output is produced by NAND gate 454 on line 152a which is provided so that the count accumulated by the counters in unit 26 is transferred to the numerical display.

V. TABLE OF COMPONENTS

In the volume ventilator, the following components have been used for the operation and function herein described.

| REFERENCE CHARACTER | COMPONENT | MODEL NO. | MANUFACTURER |
|---|---|---|---|
| 30, 33 | Spirometer & Spirometer Processor | 510 | Foregger Div. Air Products & Chemicals, Inc. |
| 80a-b, 82a-c | Display | 5082-7302 7300 Series | Hewlett Packard Corp. |
| 120,121,156, 202,204,208, 270,272,274, 276,278 | Decade Counter | SN 7490N | Texas Instruments |
| 129, 130 | Switch | IH 5018 | Intersil |
| 190,192 | Control Register | SN 7474N | Texas Instruments |
| 206,236 | Timer | LM 555CN | National Semiconductor Corp. |
| 124 | Sample & Hold | HA 2425 | Harris Semiconductor Co. |

What is claimed is:

1. A ventilator system having patient connection means and a plurality of integrated modes of operation for providing a patient with a flow of breathing gas under pressure comprising
   valve means for controlling said flow of gas to said patient connection means for inspiration and expiration,
   mode selecting means for operating said ventilator system in at least one selected mode of operation;
   adjustable setting means including a plurality of adjustable time setting means individually related to sigh inspiratory time, sigh expiratory time, inspiratory time, expiratory time and inspiratory pause time each corresponding to said integrated modes of operation with each of said time setting means producing a corresponding time related threshold signal,
   signal means including time base means for producing a common time signal which increases in value with time at a predetermined linear slope for a predetermined time duration,
   means for comparing and determining the crossing of each threshold signal with said common time signal for producing a plurality of control signals,
   means responsive to said mode selecting means for selecting at least one control signal corresponding to a selected integrated mode and for resetting the time base means to begin a new time signal thereby to provide said predetermined time duration, and means for applying said at least one selected control signal to said valve means for controlling the flow of gas to said patient connection means whereby each of said time setting means may be continuously adjusted to change one or more of said threshold signals without varying any of the other threshold signals.

2. The ventilator system of claim 1 in which said adjustable setting means includes a further adjustable time setting means related to I:E ratio for producing a corresponding threshold signal.

3. The ventilator system of claim 2 in which said comprising means includes time comparing means for comparing said time signal with each of said time related threshold signals for producing a plurality of time control signals each independent of each other and each dependent only on its respective time related threshold signal.

4. The ventilator system of claim 3 in which said time comparing means includes a plurality of comparator circuits each related to a different time related threshold signal for comparing each of said time related threshold signals with said time signal.

5. The ventilator system of claim 1 in which said comparing means including pressure comparing means for comparing said pressure signal with each of said pressure related threshold signal for producing a plurality of pressure control signals independent of each other and each dependent only on the respective pressure related threshold signal.

6. The ventilator system of claim 5 in which said pressure comparing means includes a plurality of comparator circuits each related to a different pressure related threshold signal for comparing each of said pressure related threshold signals with said pressure signal.

7. The ventilator system of claim 1 in which there is provided electronic and pneumatic malfunction alarm means including a plurality of nonadjustable alarm circuits for constant surveillance of said applying means, means for signalling upon actuation of at least one of said alarm circuits, a nonadjustable alarm condition and means coupled to each of said alarm circuits for testing said alarm circuits themselves for faults.

8. The ventilator system of claim 7 in which there is provided a power supply for said ventilator system, a first nonadjustable alarm circuit including means for indicating a nonadjustable alarm condition when at least one power supply voltage decreases beyond a predetermined threshold.

9. The ventilator system of claim 8 in which a second of said nonadjustable alarm circuits includes means for indicating a nonadjustable alarm condition when the input pressure decreases in value below a predetermined limit.

10. The ventilator system of claim 7 in which said patient malfunction alarm means includes adjustable apnea alarm means for indicating an alarm if at the end of inspiration of the patient, the pressure has not increased to the apnea threshold value.

11. The ventilator system of claim 10 in which there is provided an exhale spirometer including means for measuring the patient flow of gas coupled to said valve means, means coupled to said exhale spirometer for computing the exhale tidal volume and minute volume, and said patient malfunction alarm means including an adjustable minute volume alarm circuit including means for indicating an alarm if the value of said minute volume increases beyond or falls below predetermined values.

12. The ventilator system of claim 1 in which said electronic and pneumatic malfunction alarm means includes adjustable pressure alarm means which is activated when the pressure of said gas increases beyond a predetermined upper value.

13. The ventilator system of claim 12 in which said adjustable pressure alarm means includes means for initiating expiration of the patient immediately when said predetermined upper value is exceeded for a predetermined exhalation time.

14. The ventilator system of claim 1 in which there is provided means for computing from predetermined ones of said threshold signals values of inspiratory parameters of said ventilator system and means for displaying said parameters for observation independent of the settings of said adjustable setting means.

15. The ventilator system of claim 14 in which said computing means including first means for computing tidal volume from the threshold signals of said setting circuits related to inspiratory time and flow rate, and second means for computing breaths per minute from the threshold signals of said setting circuits related to inspiratory time and I:E ratio.

16. The ventilator system of claim 15 in which there is provided a flow transducer for sensing the exhaled flow of gas from the patient, means coupled to said transducer for computing the exhaled tidal volume and minute volume to permit the crosschecking of these values with said computed tidal time.

17. The ventilator system of claim 16 in which said valve means includes a patient circuit, said patient circuit including means for measuring the pressure of the gas close to the patient thereby avoiding excessive drops in the line.

18. The ventilator system of claim 1 in which said applying means includes means for selecting at least one of said control signals to be applied to said valve means, and there is provided mode switching means including mode selection logic means for selecting individual mode signals corresponding to sigh, assist and pause and being independent of the settings of said time related threshold signals, and means coupling said mode switching means to said selecting means for selecting at least one control signal for application to said valve means in response to said selected mode signal, without requiring any change in setting of said adjustable time setting means.

19. The ventilator system of claim 18 in which said selecting means includes bistable means for assuring said control signal is applied to said valve means for a complete breathing cycle before changing from one mode to another in response to actuation of said mode switching means.

20. An integrated ventilator system having patient connection means and a plurality of integrated modes of operation for providing a patient with a flow of breathing gas under pressure comprising mode switching means including mode selection logic means for selecting said integrated modes corresponding to sigh, assist, inspirators, pause and PEEP, valve means for controlling said flow of gas to said patient connection means for inspiration and expiration, a plurality of adjustable setting means each producing an individual predetermined threshold signal related to individual gas flow parameters of said integrated modes corresponding to sigh, assist inspiratory pause and PEEP signal sensing means coupled to said adjustable setting means for comparing said threshold signals to a reference signal for producing a plurality of control signals, and means responsive to said mode switching means for applying at least one of said control signals corresponding to a selected integrated mode to said valve means for controlling the flow of gas to said patient connection means in accordance with the selected mode whereby each of said setting means is independently adjusted and such mode selection does not require any further change in the setting of said adjustable setting means.

21. The integrated ventilator system of claim 20 in which said selecting means includes bistable means for assuring said selected control signal is applied to said valve means for a complete breathing cycle before changing from one mode to another in response to actuation of said mode switching means.

22. The integrated ventilator system of claim 20 in which there is provided means for computing from predetermined ones of said threshold signals values of inspiratory parameters of said ventilator system, and means for displaying said parameters for observation independent of the settings of said adjustable setting means.

23. The integrated ventilator system of claim 22 in which said adjustable setting means includes a plurality of adjustable setting circuits related to inspiratory time, flow rate and I:E ratio, said computing means including first means for computing tidal volume from the threshold signals of said setting circuits related to inspiratory time and flow rate, and second means for computing breaths per minute from the threshold signals of said setting circuits related to inspiratory time and I:E ratio.

24. The integrated ventilator system of claim 20 in which there is provided a flow transducer for sensing exhaled flow of gas from the patient, means coupled to said transducer for computing exhaled tidal volume and minute volume to permit the crosschecking of these values with said computed tidal volume.

25. The integrated ventilator system of claim 20 in which there is provided adjustable pressure alarm means which is activated when the pressure of said gas increases beyond a predetermined upper value.

26. The integrated ventilator system of claim 25 in which said adjustable pressure alarm means includes means for initiating expiration of the patient immediately when said predetermined upper value is exceeded for a predetermined exhalation time.

27. The integrated ventilator system of claim 20 in which there is provided adjustable apnea alarm means for indicating an alarm if at the end of inspiration of the patient the pressure has not increased to an apnea threshold value.

28. The integrated ventilator system of claim 27 in which there is provided an exhale spirometer for measuring the patient flow of gas, means coupled to said exhale spirometer for computing the exhale tidal volume and minute volume, and said patient malfunction alarm means including an adjustable minute volume alarm circuit for indicating an alarm if the value of said minute volume increases beyond or falls below predetermined values.

29. The integrated ventilator system of claim 20 in which said adjustable setting means includes a plurality of adjustable time setting means individually related to sigh, inspiratory time, inspiratory pause and I:E ratio with each of adjustable time setting means producing a corresponding time related threshold signal.

30. The integrated ventilator system of claim 29 in which there is provided a plurality of nonadjustable alarm circuits coupled to said applying means for constant surveillance of said applying means and for indicating upon actuation of at least one of said alarm circuits, a nonadjustable alarm condition.

31. The integrated ventilator system of claim 30 in which a second of said nonadjustable alarm circuits includes means for indicating a nonadjustable alarm condition when the input pressure decreases in value below a predetermined limit.

32. The integrated ventilator system of claim 31 in which a third of said nonadjustable alarm circuits includes means for indicating a nonadjustable alarm condition when said ventilator system fails to cycle between inspiration and expiration within a predetermined time duration.

33. The integrated ventilator system of claim 29 in which there is provided means for producing a time signal whose amplitude changes as a function of time, and said comparing means including time comparing means for comparing said time signal with each of said time related threshold signals for producing a plurality of time control signals each independent of each other and each dependent only on its respective time related threshold signal.

34. The integrated ventilator system of claim 20 in which said mode switching means includes a plurality of switches each corresponding to an individual sigh, assist, pause and PEEP mode signal, said selecting means including gate means coupled to said switches for selecting said control signal in accordance with said selected mode signal.

35. The integrated ventilator system of claim 20 in which said adjustable setting means includes a plurality of adjustable pressure setting means individually related to sigh pressure limit, tidal volume, normal pressure limit and assist pressure with each of said pressure setting means producing a corresponding pressure related threshold signal.

36. The integrated ventilator system of claim 35 in which there is provided means for producing a pressure signal whose amplitude changes as a function of the patient's pressure, and said comparing means including pressure comparing means for comparing said pressure signal with each of said pressure related threshold signals for producing a plurality of pressure control signals independent of each other and each dependent only on the respective pressure related threshold signal.

37. The integrated ventilator system of claim 20 in which there are provided electronic and pneumatic malfunction alarm circuits and patient malfunction alarm circuits coupled to said applying means and means coupled to said alarm circuits for testing the alarm circuits themselves for faults to determine if the alarm circuits are capable of detecting alarms.

38. A ventilator system having patient connection means and a plurality of integrated modes of operation for providing a patient having a respiratory system with a flow of breathing gas under pressure comprising valve means for controlling said flow of gas for inspiration and expiration, mode switching means including mode selection logic means for selecting said integrated modes corresponding to sigh, assist, inspiratory pause and IMV, adjustable setting means including a plurality of adjustable time setting means individually related to sigh, inspiratory time, expiratory time, and inspiratory pause with each of said time setting means producing a corresponding time related threshold signal, signal means including time base means for producing a common time signal which increases in value monotonically with time in a predetermined manner related to the respiratory system of the patient, means for comparing and determining the crossing of each threshold signal with said common time signal for producing a plurality of control signals, means responsive to said mode switching means and said comparing means for selecting at least one of said control signals corresponding to said selected integrated mode of operation, means for applying said selected control signals to said valve means for controlling the flow of gas to said patient connection, means whereby said time setting means may be continuously adjusted to change one or more of said threshold signals without varying any of the other threshold signals, and said adjustable setting means includes an adjustable IMV rate setting means for producing an IMV rate threshold, signal, means for generating an IMV reference signal, means for comparing said IMV rate threshold signal to said IMV reference signal for producing an IMV rate control signal, and means responsive to said mode switching means for applying said IMV rate control signal to said valve means when said IMV mode is selected.

39. The ventilator system of claim 38 in which there is provided variable means for producing a predetermined additional variable signal whose amplitude changes as a function of time, said IMV signal means includes a comparator circuit coupled to said variable means for comparing said IMV rate threshold signal with said additional variable signal, means for delaying the resultant signal to thereby produce said IMV rate control signal for initiating a mandatory breath when said IMV mode signal is selected.

40. The ventilator system of claim 39 in which said mode switching means includes a PEEP switch operable for selecting an individual mode signal corresponding to PEEP, PEEP means coupled to said applying means for selecting a higher positive pressure at the end of expiration of said patient for build up of the internal pressure when said PEEP mode signal is selected, and means coupled to said valve means for displaying said pressure directly connected to said patient.

41. The volume ventilator of claim 40 in which said selecting means includes means for preventing passage of all mode signals except the PEEP mode signal when said IMV mode signal is selected.

42. An integrated ventilator system having patient connection means and a plurality of integrated modes of operation for providing a patient with a flow of breathing gas under pressure comprising mode switching means including mode selection logic means for selecting individual mode signals corresponding to sigh, assist, inspiratory pause, IMV, and PEEP, valve means for controlling said flow of gas to said patient connection means for inspiration and expiration, a plurality of adjustable setting means each producing an individual predetermined threshold signal related individual flow parameters corresponding to sigh, assist, inspiratory pause, IMV and PEEP, signal sensing means coupled to said adjustable setting means for comparing said threshold signals to a reference signal for producing a plurality of control signals, means responsive to said mode switching means for applying at least one of said control signals corresponding to said selected mode of operation to said valve means for controlling the flow of gas, and said adjustable setting means including an adjustable IMV rate setting means for producing an means for comparing an IMV reference rate threshold signal, IMV signal to said IMV rate threshold signal for producing an IMV rate control signal, and means responsive to said mode switching means for applying said IMV rate control signal to said valve means when said IMV mode is selected.

43. The integrated ventilator system of claim 42 in which there is provided variable means for producing a predetermined additional variable signal whose amplitude changes as a function of time, said IMV signal means includes a comparator circuit coupled to said variable means for comparing said IMV rate threshold signal with said additional variable signal, means for delaying the resultant signal to thereby produce said IMV rate control signal for initiating a mandatory breath when said IMV mode signal is selected.

44. The integrated ventilator system of claim 43 in which said mode switching means includes PEEP switch means operable for selecting a PEEP mode signal, PEEP means coupled to said applying means for selecting a higher positive pressure at the end of expiration of said patient for build up of the internal pressure when said PEEP mode signal is selected, and means coupled to said valve means for displaying said pressure directly connected to said patient.

* * * * *

UNITED STATES PATENT AND TRADEMARK OFFICE
CERTIFICATE OF CORRECTION

PATENT NO. : 4,323,064
DATED : April 6, 1982
INVENTOR(S) : Richard J. Hoenig and James J. Klinikowski It is certified that error appears in the above-identified patent and that said Letters Patent are hereby corrected as shown below:

In claim 42, lines 32 and 33, delete "means for comparing an IMV reference" and insert --IMV--;

line 34, delete "IMV" (first occurrence) and insert --means for comparing an IMV reference--.

Signed and Sealed this

Fifteenth Day of February 1983

[SEAL]

Attest:

GERALD J. MOSSINGHOFF

Attesting Officer  Commissioner of Patents and Trademarks